(12) United States Patent
White et al.

(10) Patent No.: US 9,395,287 B2
(45) Date of Patent: Jul. 19, 2016

(54) MOBILE TEST SYSTEM AND METHODS FOR IN SITU CHARACTERIZATION OF STRESS AND DEFLECTION DEPENDENT STIFFNESS AND BEARING CAPACITY OF SOILS AND GEO-MATERIALS

(71) Applicants: David Joshua White, Boone, IA (US); Robert Frank Steffes, Ames, IA (US); Ells Thomas Cackler, Ames, IA (US)

(72) Inventors: David Joshua White, Boone, IA (US); Robert Frank Steffes, Ames, IA (US); Ells Thomas Cackler, Ames, IA (US)

(73) Assignee: INGIOS GEOTECHNICS, INC., Boone, IA (US)

( * ) Notice: Subject to any disclaimer, the term of this patent is extended or adjusted under 35 U.S.C. 154(b) by 111 days.

(21) Appl. No.: 13/857,525

(22) Filed: Apr. 5, 2013

(65) Prior Publication Data

US 2013/0283925 A1    Oct. 31, 2013

Related U.S. Application Data

(60) Provisional application No. 61/621,059, filed on Apr. 6, 2012.

(51) Int. Cl.
    *G01N 3/10*      (2006.01)
    *G01N 3/00*      (2006.01)
    *E02D 1/04*      (2006.01)
    *G01N 3/40*      (2006.01)

(52) U.S. Cl.
    CPC .. *G01N 3/10* (2013.01); *E02D 1/04* (2013.01); *G01N 3/40* (2013.01)

(58) Field of Classification Search
    CPC ............... G01N 3/10; G01N 3/40; E02D 1/04
    USPC ....................... 73/784, 594, 146, 78
    See application file for complete search history.

(56) References Cited

U.S. PATENT DOCUMENTS

| | | | |
|---|---|---|---|
| 3,813,929 | A | 6/1974 | Hardin et al. |
| 4,116,041 | A | 9/1978 | Tholen et al. |
| 6,513,384 | B1 | 2/2003 | Quibel et al. |

(Continued)

FOREIGN PATENT DOCUMENTS

| | | |
|---|---|---|
| DE | 693 00 731 T2 | 5/1996 |
| GB | 2 249 181 A | 4/1992 |

OTHER PUBLICATIONS

Extended European Search Report dated Nov. 10, 2015 for European Patent Application No. 13773150.1.
First Examination Report for New Zealand Patent Application No. 701640 dated Aug. 26, 2015.

(Continued)

*Primary Examiner* — Harshad R Patel
*Assistant Examiner* — Brandi Hopkins
(74) *Attorney, Agent, or Firm* — Olive Law Group, PLLC

(57) ABSTRACT

An integrated mobile test system and methods for characterizing in situ stress or strain/deflection—dependent stiffness and bearing capacity enables the testing of engineering properties of natural, compacted, stabilized, and reinforced soils and geo-materials. The mobile test system and associated methods (1) prepare the ground for testing and (2) apply static or cyclic loading to one or more bearing plates of various geometries positioned at the ground surface or below the ground surface to determine both stress and deflection dependent stiffness relationships and the bearing capacity of the soil or geo-material. Optionally, the mobile test system and associated methods (3) apply ground confining stress conditions independent of the bearing plate loading.

28 Claims, 24 Drawing Sheets

(56) References Cited

U.S. PATENT DOCUMENTS

| | | |
|---|---|---|
| 6,604,432 B1 | 8/2003 | Hamblen et al. |
| 2004/0163448 A1 | 8/2004 | Hage et al. |
| 2008/0184808 A1 | 8/2008 | Berra |
| 2009/0204344 A1 | 8/2009 | Daraio |

OTHER PUBLICATIONS

Response to Examination Report for New Zealand Patent Application No. 701640 dated Mar. 24, 2016.

Patent Examination Report No. 1 dated Apr. 6, 2012 in Australian Patent Application 2013243286.

PCT Search Report and Written Opinion for PCT International Application PCT/US2013/035458, related application, dated Apr. 5, 2013.

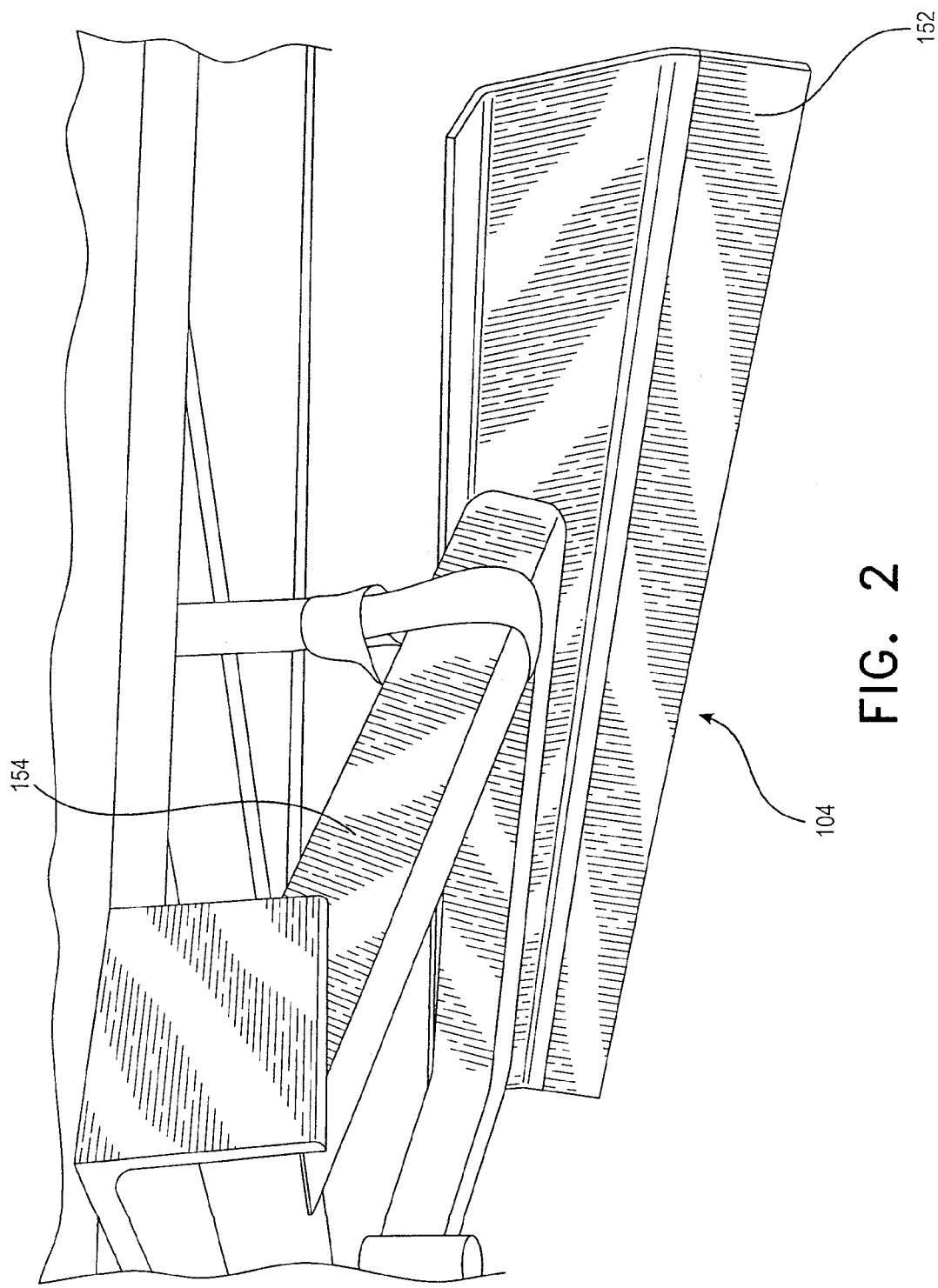

Example test results for curved plate bearing test with no confinement: plate contact stress versus deformation plot Example of incremental static test results for flat plate bearing test without confinement: (a) Stress versus deflection response Example of incremental static test results for flat plate bearing test without confinement: (b) deflection versus time response Example of mathematics relationship between in situ resilient modulus and bulk stress for tests performed with 12 combinations of plate stress and confining stress

| Sequence | Surface Confinement (psi) | Max Stress (psi) | Cyclic Stress (psi) | Number of Cycles |
|---|---|---|---|---|
| condition 0 | 10 | 20 | 10 | |
| 1 | 2 | 12.5 | 2.5 | |
| 2* | | 20 | 10 | |
| 3* | | 30 | 20 | |
| 4* | 3.3 | 40 | 30 | |
| 5* | | 50 | 40 | |
| 6 | 6.7 | 12.5 | 2.5 | |
| 7* | | 20 | 10 | 20 |
| 8* | | 30 | 20 | |
| 9* | | 40 | 30 | |
| 10* | 10 | 50 | 40 | |
| 11* | | 20 | 10 | |
| 12* | | 30 | 20 | |
| 13* | 13.3 | 40 | 30 | |
| 14* | | 50 | 40 | |
| Note: * indicates sequences used in calculating in situ resilient modulus model parameters | | | | |

FIG. 18(b)

MOBILE TEST SYSTEM AND METHODS FOR IN SITU CHARACTERIZATION OF STRESS AND DEFLECTION DEPENDENT STIFFNESS AND BEARING CAPACITY OF SOILS AND GEO-MATERIALS

CROSS-REFERENCE TO RELATED APPLICATION

This application claims the benefit of priority to U.S. Provisional Application for Patent No. 61/621,059 filed Apr. 6, 2012.

BACKGROUND OF THE INVENTION

1. Field of Invention

The present invention relates to an apparatus and associated methods for the in situ testing of engineering properties of soils and geo-materials. More specifically, the present invention relates to a mobile test system and associated test methods that determine in situ the stiffness and bearing capacity of soils and geo-materials.

2. Description of the Prior Art

The construction of civil infrastructure such as pavements, embankments, railway beds, airfield, walls, and industrial and commercial buildings typically requires a determination of soil engineering properties for construction verification and design purposes. These properties include the static or cyclic stress-dependent stiffness and bearing capacity of the soil. Although used for design, during construction these parameter values are not regularly measured as part of field quality control and quality assurance inspection processes due to lack of suitable field equipment and methods. Thus, construction processes are not field controlled to achieve the directly measured values provided in design documents. Instead, the construction processes rely on indirect measurement (e.g., California bearing ratio (CBR), density, dynamic cone penetrometer and falling weight deflectometer).

Recently, new design methods for pavement systems, for example, require selection of stress-dependent stiffness values of the pavement foundation layers to determine the pavement thickness. Soil stabilization and reinforcement via compaction and/or chemical and mechanical stabilization are being used to improve the in situ characteristics of soil and geomaterials to achieve the desired in situ stiffness. The in situ characterization methods typically rely on longstanding measurements of weight and volume relationships. However, the aforementioned methods do not characterize the static or cyclic stress and deflection dependent stiffness and bearing capacity.

It is known in the art to determine the in situ static or dynamic stress-dependent stiffness using deflectometers. For example, U.S. Pat. No. 4,116,041 to Tholen et al. discloses the use of a falling weight to transmit shock energy to a pressure plate engaged on the ground. Another example of in situ stiffness determination is U.S. Pat. No. 6,604,432 to Hamblem et al., which discloses the use of a portable apparatus that determines the shear modulus of the surface layer to determine soil compaction.

However, a disadvantage of these conventional test methods is that they (i) do not provide measurements under static conditions, (ii) only use a flat plate or a ring for transmitting the load to the ground, (iii) are only suitable for selected material conditions due to limits in the sensor systems, (iv) do not provide for confining stress control around the loading area, and (v) do not allow for strain or deflection controlled testing.

Therefore, a need exists for improved measurement techniques for determining in situ the stress and deflection dependent stiffness relationships and bearing capacity for a wide range of materials and conditions associated with various soils and geo-materials.

SUMMARY OF THE INVENTION

The present invention overcomes the above-described limitations of the prior art by providing an apparatus and associated methods for in situ testing of the engineering properties of natural, compacted, stabilized, and reinforced soils and geo-materials. More specifically, the present invention provides an integrated mobile test system and associated test methods for the in situ characterization of the stress and deflection dependent stiffness and bearing capacity of soils and geo-materials.

According to a preferred embodiment of the present invention, the mobile test system (1) prepares the ground for testing and (2) applies static or cyclic loading to one or more bearing plates of various geometries positioned at the ground surface or below the ground surface to determine stress and deflection dependent stiffness relationships and bearing capacity of the soil or geo-material. Optionally, the mobile test system (3) applies ground confining stress conditions independent of the bearing plate loading.

According to the preferred embodiment, the mobile test system includes a trailer-mounted test apparatus that provides reaction weight, with supplementary ballast boxes and a tie-down anchoring system for additional reaction weight; a hydraulic piston with control system and derrick frame for applying static and cyclic loads; a quick assembly reference beam for bearing plate position measurements and deflection controlled testing; a moveable counterbalance weight system for balancing the trailer system prior to bearing plate loading; an integrated plow to prepare the ground for testing; a hydraulic or pneumatic confining plate system to optionally control ground stresses independent of the bearing plate stresses; and bearing plates of various geometries that induce controlled stress magnitude and stress orientation in the test materials.

According to one aspect of the invention, the mobile test system provides a level and balanced reaction to maximize the imparted reaction load on the ground. The trailer system is leveled with outrigger hydraulic jacks and balanced front-to-back with the moveable counterbalance weight system. Integrated level sensors provide feedback to a hydraulic control system to automate the trailer leveling process.

According to another aspect of the invention, the ground is prepared for testing using the trailer integrated plow system. The plow is engaged with the ground to prepare a flat surface free from debris at the desired depth.

According to yet another aspect of the invention, the bearing plate assemblies are moved under the hydraulic piston and derrick by a moveable tray integrated with a moveable counterweight assembly, and lifted off the tray by the hydraulic piston and lowered to the ground for testing.

According to a further aspect of the invention, the confining plate assembly attached to the moveable tray is secured to hydraulic or pneumatic pistons and pressed onto the ground to provide controlled stress conditions around the perimeter of the bearing plate. A control system provides a constant confining stress during bearing plate loading allowing for ground contraction or expansion as a result of material movement around the bearing plates and volume changes during loading such as occurs due to ground consolidation or dilation.

According to a still further aspect of the invention, the bearing plates are attached to the hydraulic piston assembly using a common adapter plate and connector.

According to another aspect of the invention, the bearing plate geometries include flat, conical, spherical, wedge, conical frustum, truncated frustum, and cycloid shapes. The bearing plate shape is selected to achieve the desired stress orientations, i.e., vertical, horizontal, radial, tangential, and circumferential, in the test materials.

According to yet another aspect of the invention, the bearing plates are pushed onto the ground surface under controlled static loading conditions while the bearing plate position is monitored using the reference beam assembly. The tests can be automated to control the static loading events based on the desired bearing plate contact stress, deflections, or deflection rate to simulate various foundation and pavement loading conditions.

According to an additional aspect of the invention, the bearing plates are pushed onto the ground surface with confining stress being applied to the ground surface by the confining plate assembly reacting against the test trailer. By performing plate bearing tests at multiple plate confining stresses and plate contact stresses, a mathematical relationship between ground stiffness and confinement stress, bulk stress, and/or octahedral stress can be determined.

According to still another aspect of the invention, tests are performed by creating a cavity in the ground and testing below the surface.

According to yet another aspect of the invention, the bearing plates are pushed onto the ground surface under controlled static or cyclic strain/deflection values by monitoring bearing plate position using the reference beam assembly.

According to another aspect of the invention, soil samples can be collected at the bearing plate test locations by using the piston and derrick assembly to push thin-walled tube samplers into the test material.

According to another aspect of the invention, the method associated with the mobile test system includes a method for performing static bearing plate tests with or without confinement control. The method includes (a) preparing the ground surface using the integrated plow system; (b) positioning the plate assembly on or in the ground; and (c) applying controlled loads using the hydraulic control system, or controlled deflection test operations using the vertical deformation response during loading. Controlled deflection test operations are possible by increasing or decreasing the hydraulic piston down force on the bearing plate to achieve the desired bearing plate deflection. Once the predetermined deflection value is achieved, the piston force is adjusted accordingly. Optionally, the method includes (d) applying controlled ground confinement using the integrated confinement plate system.

According to still another aspect of the invention, the method associated with the mobile test system includes a method for performing cyclic bearing plate tests with or without confinement control. The method includes (a) preparing the ground surface using the integrated plow system; (b) positioning the plate assembly on or in the ground; and (c) applying controlled load-unload cycles (stress magnitude and load-unload durations) using the hydraulic control system, or controlled deflection test operations using the vertical deformation response during loading. Optionally, the method includes (d) applying controlled ground confinement using the integrated confinement plate system.

In view of the foregoing, it is therefore an object of the present invention to provide an integrated mobile test system for characterizing in situ the stress or deflection dependent stiffness and bearing capacity of soils and geo-materials.

Another object of the invention is to provide a mobile test system that (1) prepares the ground for testing and (2) applies static or cyclic loading to one or more bearing plates of various geometries positioned at the ground surface or below the ground surface to determine in situ stress and deflection dependent stiffness relationships and bearing capacity of the soil or geo-material. Optionally, the mobile test system (3) applies ground confining stress conditions independent of the bearing plate loading.

Still another object of this invention is to provide a mobile test system that includes a trailer-mounted test apparatus that provides reaction weight, with supplementary ballast boxes and a tie-down anchoring system for additional reaction weight; a hydraulic piston with control system and derrick frame for applying static and cyclic loads; a quick assembly reference beam for bearing plate position measurements and deflection controlled testing; a moveable counterbalance weight system for balancing the trailer system prior to bearing plate loading; an integrated plow to prepare the ground for testing; a hydraulic or pneumatic confining plate system to optionally control ground stresses independent of the bearing plate stresses; and bearing plates of various geometries that induce controlled stress magnitude and stress orientation in the test materials.

Another object of this invention is to provide in situ soil and geo-material characterization test methods for use with the integrated mobile test system.

More specifically, an object of the invention is to provide improved measurement techniques for determining in situ the stress and deflection dependent stiffness relationships and bearing capacity for a wide range of materials and conditions associated with various soils and geo-materials.

Therefore, yet another object of the invention is to provide a method for performing static plate bearing tests with or without confinement control, and a method for performing cyclic plate bearing tests with or without confinement control.

These together with other objects and advantages which will become subsequently apparent reside in the details of construction and operation as more fully hereinafter described and claimed, reference being had to the accompanying drawings forming a part hereof, wherein like reference numbers refer to like parts throughout. The accompanying drawings are intended to illustrate the invention, but are not necessarily to scale.

BRIEF DESCRIPTION OF THE DRAWINGS

FIG. 2 is a perspective view of an integrated plow assembly of the mobile trailer system shown in FIG. 1.

DETAILED DESCRIPTION OF THE PREFERRED EMBODIMENTS

Figure 1:
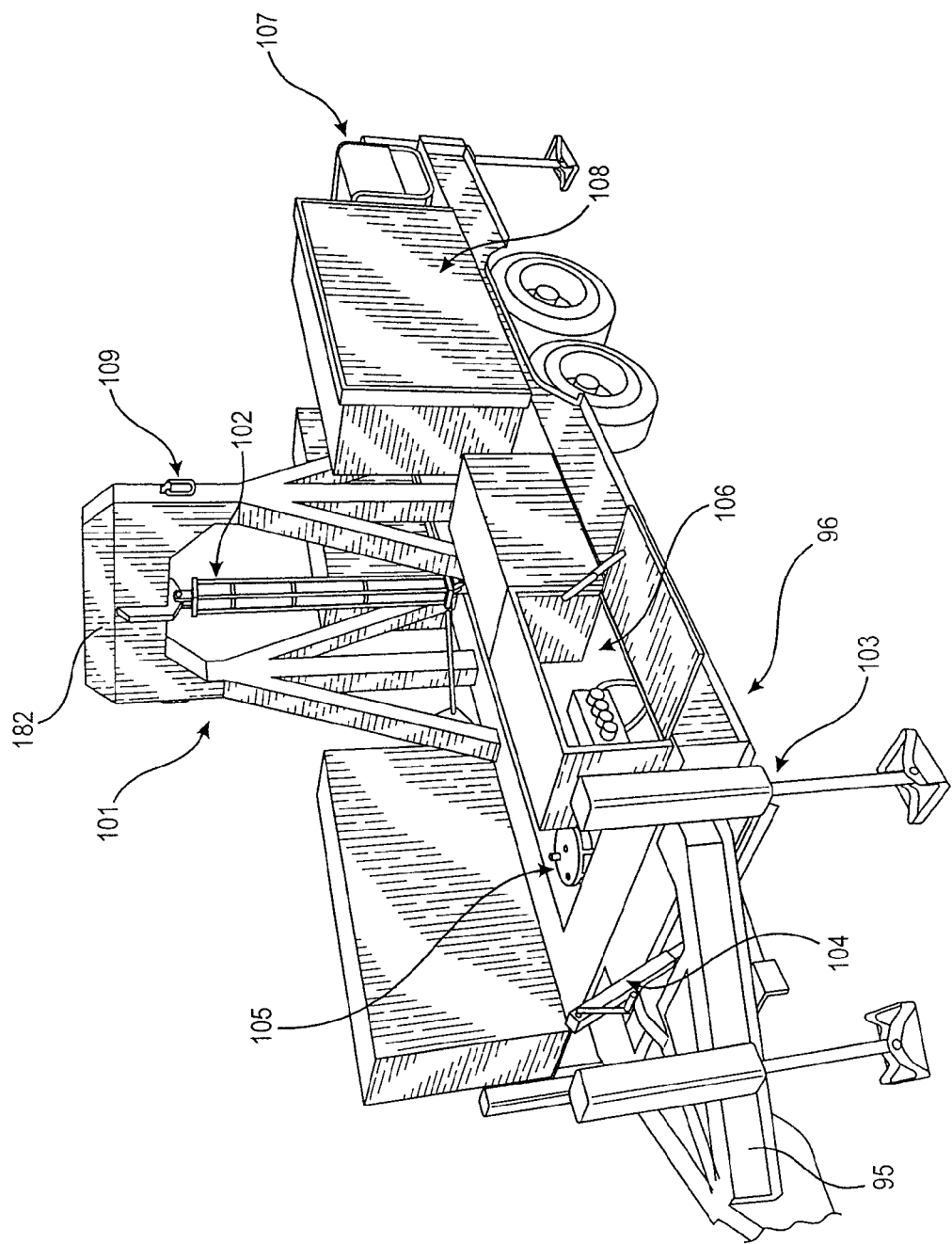
FIG. 1 is a perspective view of a mobile trailer system in accordance with an embodiment of the present invention.

Although preferred embodiments of the invention are explained in detail, it is to be understood that other embodiments are possible. Accordingly, it is not intended that the invention is to be limited in its scope to the details of construction, and arrangement of components set forth in the following description or illustrated in the drawings. The invention is capable of other embodiments and of being practiced or carried out in various ways. Also, in describing the preferred embodiments, specific terminology will be resorted to for the sake of clarity. It is to be understood that each specific term includes all technical equivalents that operate in a similar manner to accomplish a similar purpose. Where possible, components of the drawings that are alike are identified by the same reference numbers.

In general, the present invention is directed to a mobile test system and associated test methods that (1) prepare ground for testing and (2) apply controlled static or cyclic loading to one or more bearing plates of various geometries positioned at the ground surface or below the ground surface to determine stress and deflection dependent stiffness relationships and bearing capacity. Optionally, the mobile test system and associated test methods (3) apply ground confining stress conditions independent of the bearing plate loading.

Figure 17:
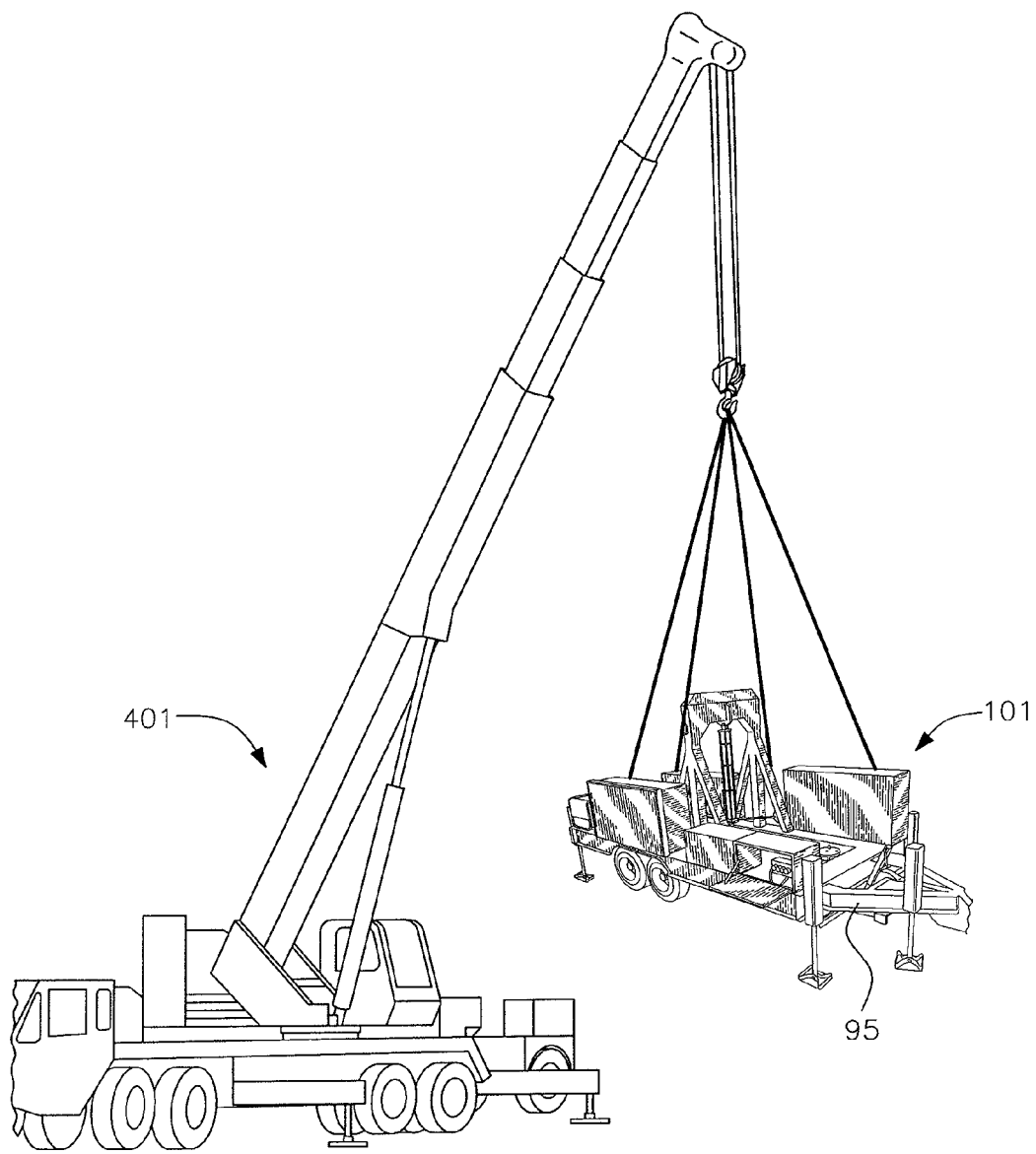
FIG. 17 is a perspective view of a crane being used for positioning the mobile trailer system shown in FIG. 1.

Referring now specifically to FIG. 1 of the drawings, a mobile test system in accordance with one embodiment of the present invention is generally designated by reference number 101. In this embodiment, the mobile test system 101 is configured as a trailer 95. The trailer 95 can be positioned by a tow vehicle, or can be picked up and placed using a crane 401 (see FIG. 17). The trailer 95 includes a hydraulic piston and derrick assembly 102 capable of handling vertical loads of up to 40,000 pounds or more. The hydraulic piston and derrick assembly 102 is connected with a pin connection and reinforced with steel tubing and anchored to the trailer inner and outer side channel members 150. See FIG. 3.

Prior to testing, the surface of the ground to be tested is prepared to be both flat and clean of loose debris, preferably using an integrated plow assembly 104 located ahead of the hydraulic piston and derrick assembly 102. FIGS. 1 and 2 show the plow assembly 104 that is integrated into the underside of the trailer 95. The plow assembly 104 includes a plow blade 152 and a plow carriage 154. The plow blade 152 is positioned with a hand crank to engage the ground. The trailer 95 is pulled forward while the plow blade 152 is engaged with the ground. One or more passes of the plow blade 152 creates a ground surface that is both clean of debris and flat for testing at the desired depth. In the particular embodiment depicted in FIGS. 1 and 2, the width of the plow blade 152 is 72 inches. However, the plow blade width can be narrower or wider, depending upon the particular application, and a plow blade or other ground preparation mechanism does not have to be integral with the mobile test system.

Once the ground surface has been prepared, the trailer is leveled using outrigger jacks. More specifically, with automated hydraulic control system 106, hydraulic leveling jacks 103 located at the four corners and tongue of the trailer are used to level the trailer 95 for testing. The hydraulic jacks 103 are positioned to be outside a zone of influence developed from the bearing plate tests. The zone of influence is the area under and around the bearing plate that is subject to deflection (the zone is sometimes also known as a deflection basin). Soil around the periphery of the bearing plate gets pulled down with the plate, but to a lesser amount with increasing radial distance from the edge of the bearing plate forming the deflection basin. The point of reference for monitoring bearing plate deflection needs to be outside this zone of influence.

The hydraulic jacks 103 are used to lift the wheels of the trailer off the ground such that loads associated with the trailer wheels do not influence the test measurements.

Next, the trailer 95 is balanced front to rear using a moveable counterweight assembly 105 integrated with a moveable tray 205. The moveable tray 205 moves the bearing plates 111 into position for connecting to the hydraulic piston. The counterweight assembly 105 provides weight balance for the trailer 95. See FIGS. 1 and 3A, 3B. The counterweight assembly 105 is positioned near the trailer axles during a transport mode to minimize trailer tongue weight, and is secured with removable steel pins through a guide rail system and a brake system (not shown). However, when preparing for testing use, the moveable counterweight assembly 105 is moved to the front of the trailer 95. The counterweight assembly 105 is pulled to the front 96 of the trailer 95 after leveling using a detachable pull bar or an electric powered motor system (not shown).

The counterweight assembly 105 is moved to the front of the trailer 95 for testing purposes because the move shifts the center of gravity of the trailer reaction to the region of the piston and derrick assembly 102. The term "trailer reaction" refers to the weight of the trailer that counteracts the down force of the hydraulic ram on the bearing plate. By moving the counter weight, the down force on the ram can be maximized.

Figure 3A:
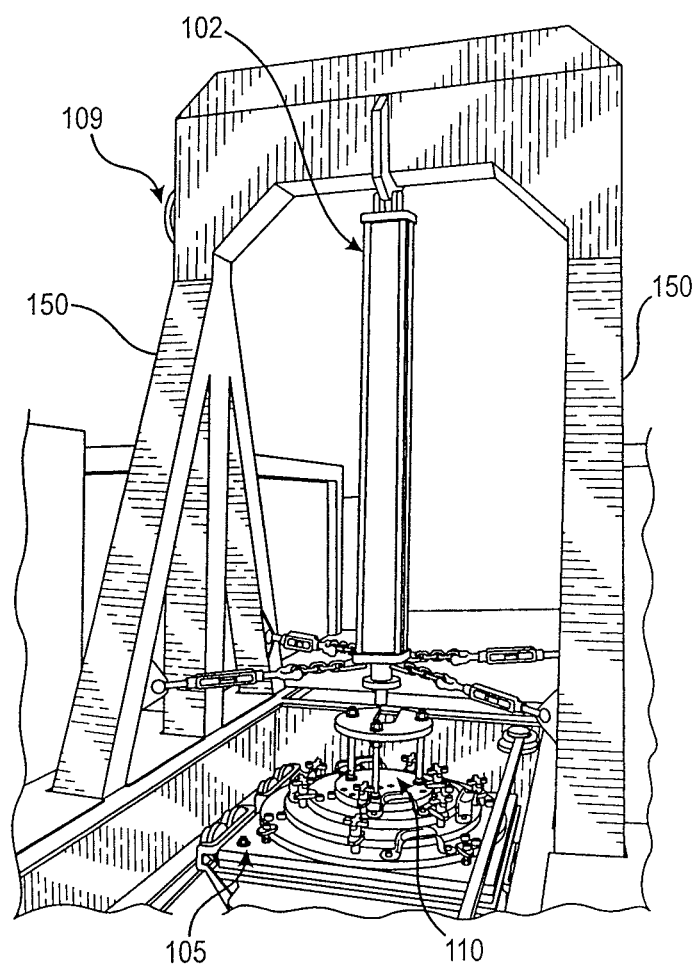
FIG. 3A is a perspective view of a derrick/piston assembly, a bearing plate assembly, and a moveable counterbalance assembly of the mobile trailer system shown in FIG. 1.
Figure 3B:
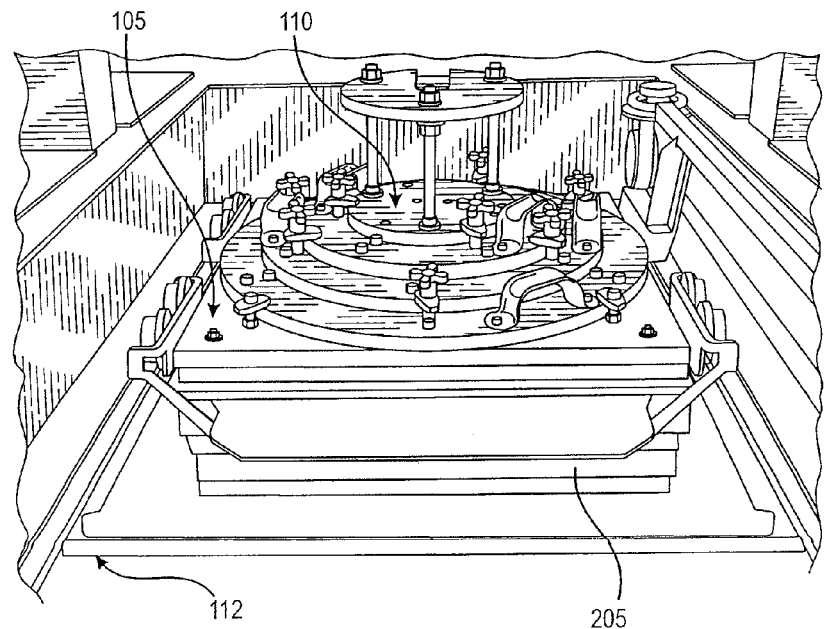
FIG. 3B is an enlarged perspective view of the moveable counterbalance assembly and bearing plate assembly shown in FIG. 3A, and a confining plate assembly.

The counterweight assembly 105 associated with the embodiment of the invention depicted in FIGS. 1 and 3A, 3B weighs approximately 2500 pounds. However, the counterweight assembly 105 can be heavier or lighter, depending upon the particular application and trailer configuration.

Figure 4A:
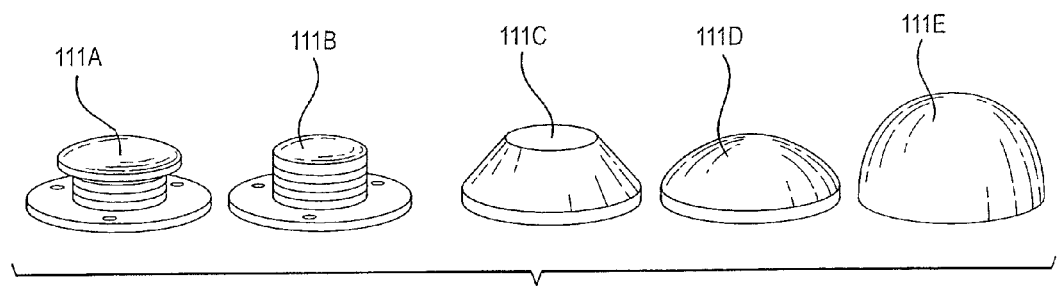
FIG. 4A is a perspective view of various bearing plate geometries associated with the bearing plate assembly shown in FIGS. 3A and 3B.
Figure 4B:
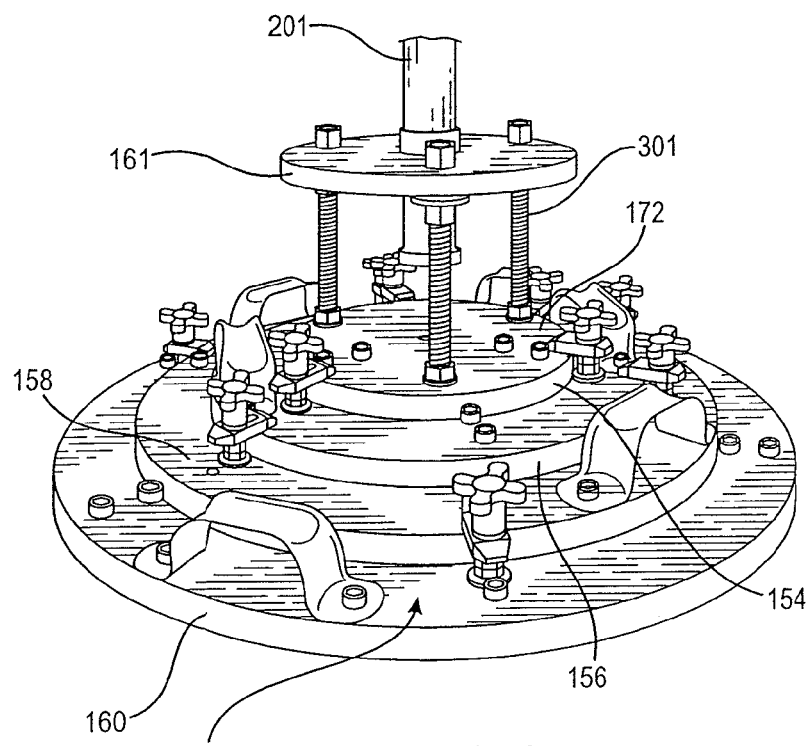
FIG. 4B is an enlarged perspective view of the bearing plate assembly shown in FIGS. 3A and 3B.

The counterweight assembly 105 also carries the bearing plate assembly 110 shown in FIGS. 3A, 3B, and 4B. In FIG. 3B, the bearing plate assembly 110 is shown on the counterweight assembly 105 with the counterweight assembly in the forward position. The bearing plate assembly 110 is typically only in this forward position temporarily, for example, when it is being changed out, i.e., receiving a different bearing plate(s). During transport of the trailer 95, the bottom side of the counterweight assembly 105 is also used to carry a confining plate assembly 112 (discussed below) shown in FIGS. 5A and 5B.

The reaction weight needed for the testing, typically up to 40,000 pounds of reaction load, is provided by the deadweight of the mobile trailer 95, and optionally, by the weight of ballast boxes 108 and the weight associated with attachments to a tie-down system that includes the tie-down anchors 109. One embodiment of the tie-down system for added weight positions the tie-down anchors 109 near the center of gravity lengthwise of the hydraulic piston and derrick assembly 102. Another embodiment of the tie-down system positions the tie-down anchors 109 at the corners of the trailer 95.

Figure 8A:
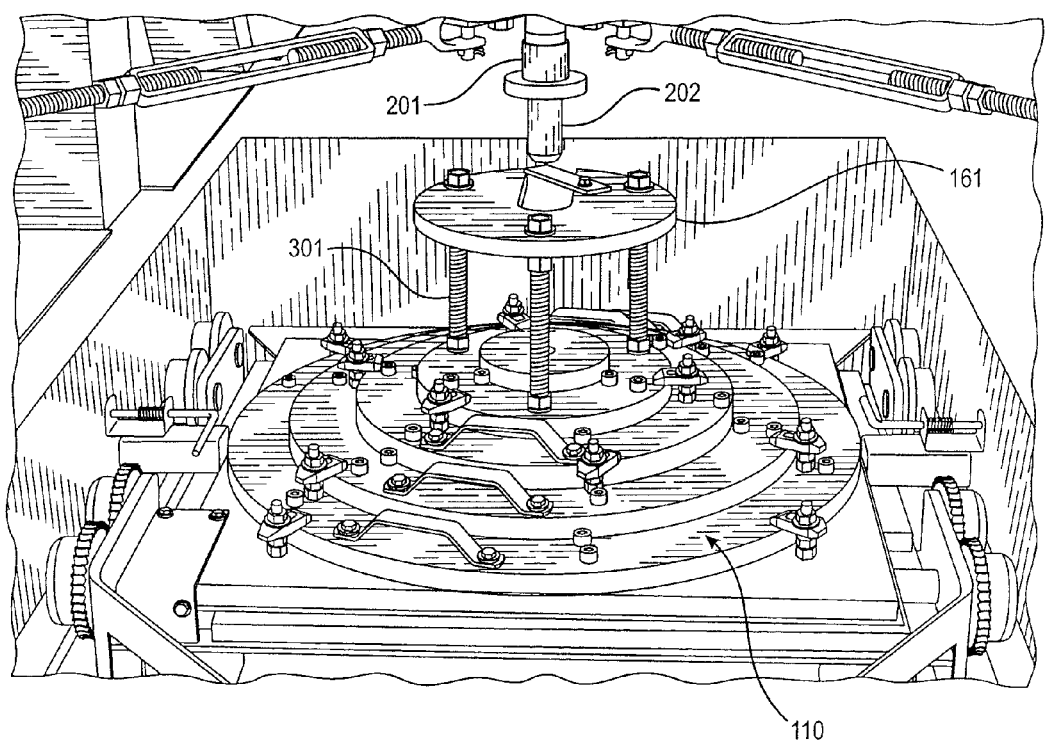
FIG. 8A is a top perspective view of the bearing plate assembly shown in FIGS. 3A, 3B, and 4B shown in conjunction with a piston collar associated with the piston of the piston/derrick assembly.
Figure 8B:
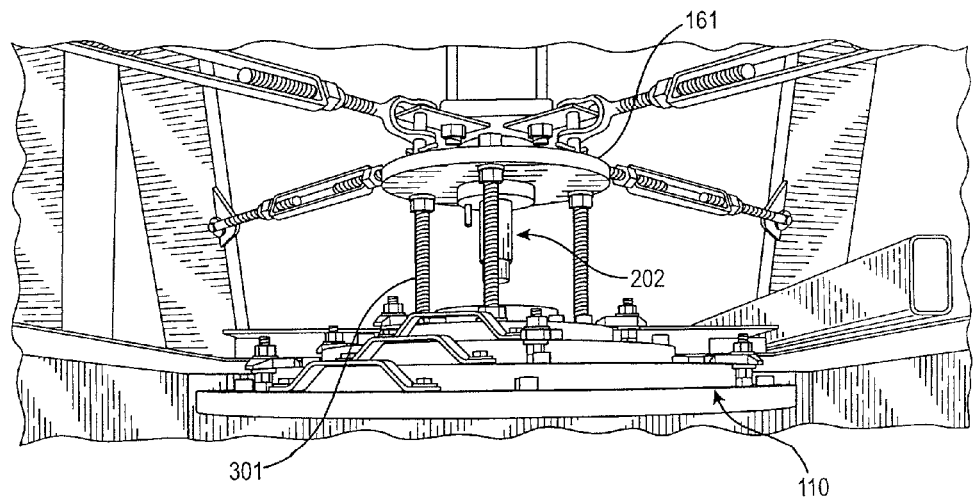
FIG. 8B is a lower perspective view of the bearing plate assembly shown in FIG. 8A shown in conjunction with the piston collar.

For testing, the bearing plate assembly 110 is connected to the hydraulic piston (also referred to as "hydraulic ram") and derrick assembly 102, and is lowered to the ground surface. The hydraulic piston and derrick assembly 102 includes, as shown in FIGS. 8A and 8B, a piston 201 and a piston collar 202.

Figure 10:
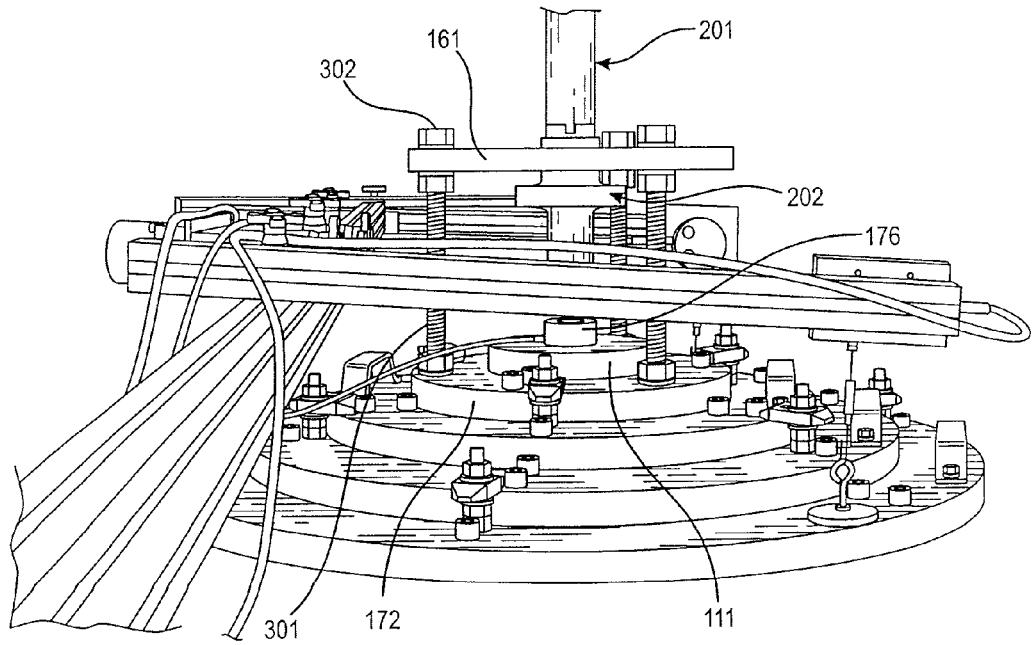
FIG. 10 is a perspective view of the load cell shown in FIG. 9 in conjunction with the bearing plate assembly and piston shown in FIGS. 8A and 8B.

The bearing plate assembly 110 includes generally an adapter plate 161, an integrated pick up plate 172, and one or more bearing plates 111. The integrated pick up plate 172 mates directly with the bearing plates 111 through a plurality of vertically oriented steel rods (i.e., bolts) 301 secured with threaded connectors 302 (see, e.g., FIGS. 4B, 6, and 10).

FIG. 4A shows five steel bearing plate configurations 111A-E of sizes ranging from 6 inches in diameter to 12 inches in diameter having, respectively, a flat shape (111A and 111B), the shape of a truncated conical frustum (111C), a partial hemispherical shape (111D), and a hemispherical shape (111E). In general, the bearing plate geometries can include flat, conical, spherical, wedge, conical frustum, truncated frustum, and cycloid shapes. The bearing plate shape is selected to achieve the desired stress orientations, i.e., vertical, horizontal, radial, tangential, and circumferential, in the test materials.

FIG. 4B shows the bearing plate assembly 110 made up of a stack of 1-inch thick steel plates of 12, 18, 24, and 30 inch diameters, reference numbers 154, 156, 158, and 160, respectively. The dual 12-inch plate assembly includes a top plate, i.e., adapter plate 161, to act as a guide for the extended piston 201 during testing and as a pick up for the end of the piston via piston collar 202 (see FIG. 13B). The adapter plate 161 includes a centered slot that fits around the piston collar 202. The piston collar 202 is attached directly to the bottommost end of the hydraulic piston 201. Again, see FIG. 8B.

The mobile test system 101 is capable of applying a wide range of stress values to the ground. The stress that the mobile test system applies to the ground depends on the size and shape of the bearing plate, and the load that is applied thereto. For example, according to the present invention, for a 12 inch diameter bearing plate, the stress value that can be applied ranges from about 0 to about 350 pounds per square inch.

Figure 4C:
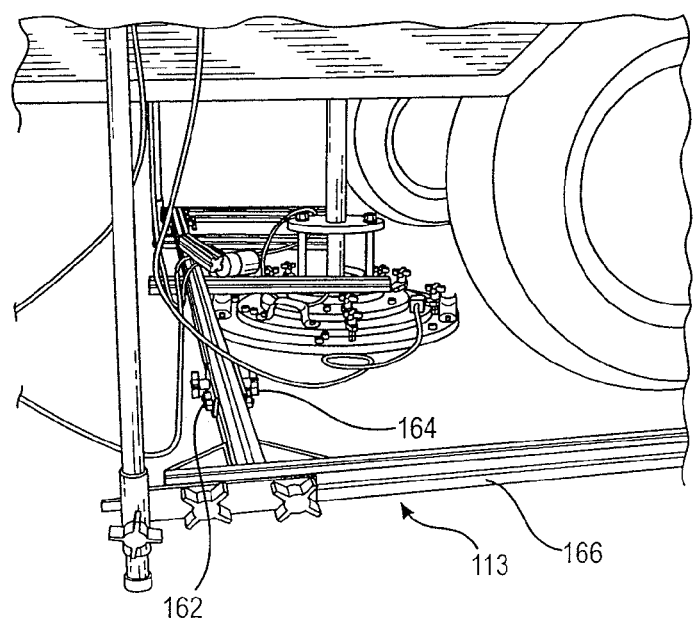
FIG. 4C is a perspective view of a reference beam assembly of the mobile trailer system shown in FIG. 1.
Figure 6:
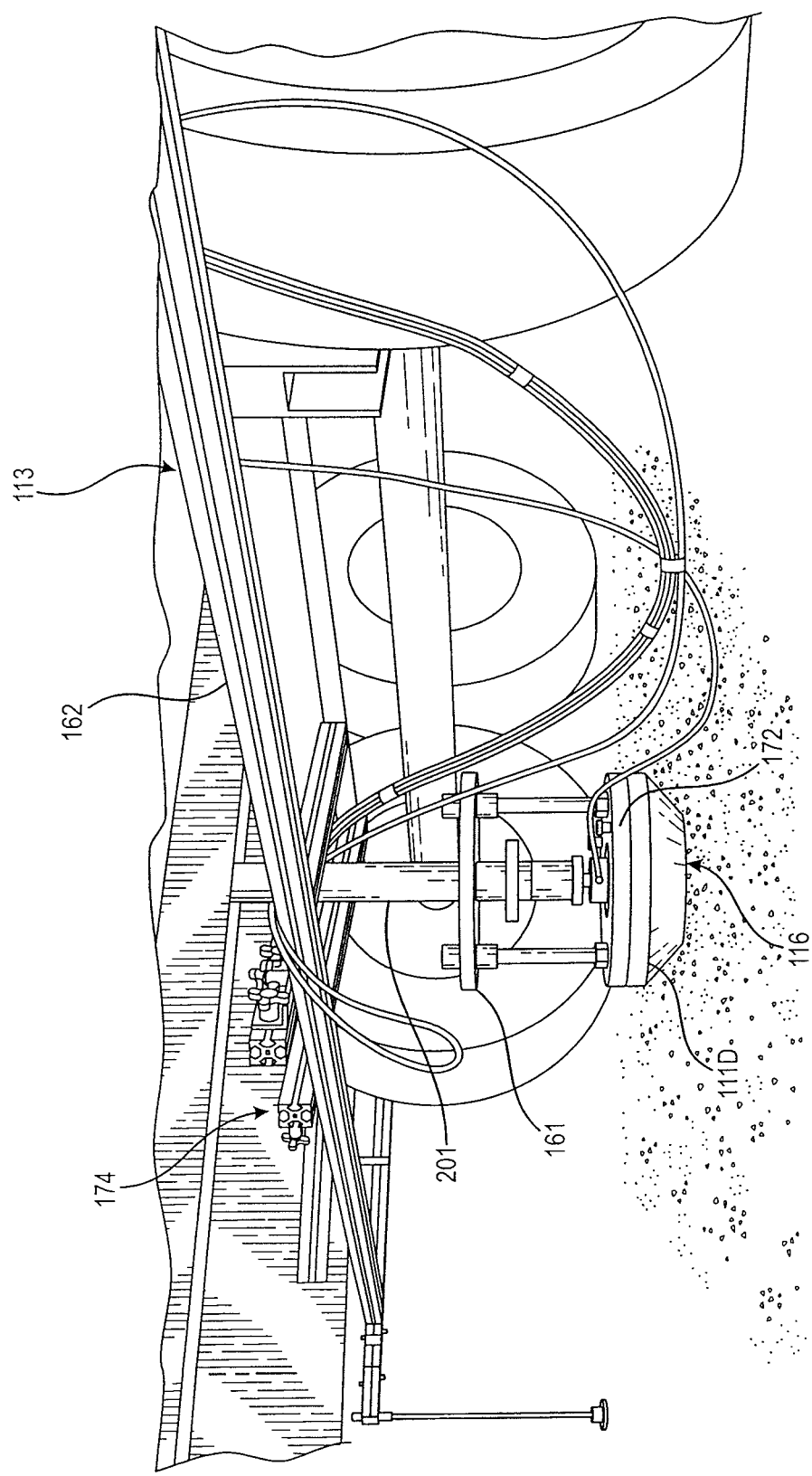
FIG. 6 is a perspective view of a 300 mm curved bearing plate associated with the reference beam assembly shown in FIG. 4C.

FIG. 4C shows the quick assembly reference beam assembly 113. The reference beam assembly 113 is positioned ahead of the bearing plate assembly 110 (i.e., in the direction toward the front 96 of the trailer 95) and is used to determine the position, i.e., the vertical position/movement, as a result of applying various static or cyclic loads to the bearing plate. The reference beam assembly 113 includes generally a reference beam 162 (FIGS. 4C and 6), reference beam extension arms 117 (FIG. 6), and deflection sensors 174 (FIG. 6). As shown in FIG. 4C, the reference beam 162 includes a cross member beam 164 and end members 166.

The reference beam 162 is stiff enough to provide a stable reference point for attaching the deflection sensors 174 that measure bearing plate position during loading. The cross member beam 164 is long enough to be outside the deflection basin of the bearing plate test (typically about 4 feet from the edge of a bearing plate). The cross member beam 164 attaches at each end thereof to the end members 166. The deflection sensors 174 are attached to the extension members 117 that are fixed to the cross member beam 164. The position of the deflection sensors 174 (typically, three sensors spaced at equidimensional distance from the center of the bearing plate and/or one at the center of the plate) is adjustable vertically and horizontally. A comparison of the vertical deflection at the center of the plate and at the edges is used to determine plate bending for various plate sizes and loads.

In general, if desired, the testing of the soils and geomaterials can be conducted with ground confinement provided by a confining plate that is pressed onto the ground with an integrated hydraulic or pneumatic control system reacting against the trailer. The hydraulic or pneumatic control system maintains constant confining stress at the ground contact during testing and accounts for ground movement during loading of the bearing plate. Various plate geometries can be used to control the stress magnitudes and orientations at the ground plate interface. And, the bearing plate tests can be performed with either controlled stress conditions for static or cyclic loading, or with controlled deflections for static or cyclic loading.

Loading operations for static loading involve applying increasing increments of down force on the bearing plate via the hydraulic piston and allowing a given increment of down force to remain constant until practically complete deformation has taken place. Then, the next increment of load is applied, etc. Load increments are typically selected based on the desired plate contact stress. The static loading protocol is described in American Association of State Highway and Transportation Officials ("AASHTO") T222, entitled "Non-repetitive Static Plate Load Test of Soils and Flexible Pavement Components for Use in Evaluation and Design of Airport and Highway Pavements," the subject matter of which is hereby expressly incorporated by reference as if fully set forth herein in its entirety.

Cyclic tests are conducted by applying a repeated load pulse (i.e., a short duration load/unload event). During testing the ground under the bearing plate is subjected to cyclic stresses. A laboratory version of a similar test sequence is described in AASHTO T307, entitled "Determining the Resilient Modulus of Soils and Aggregate Materials," the subject matter of which is hereby expressly incorporated by reference as if fully set forth herein in its entirety. For both the static and cyclic tests, the applied force can range from 0 to about 40,000 pounds.

Figure 5A:
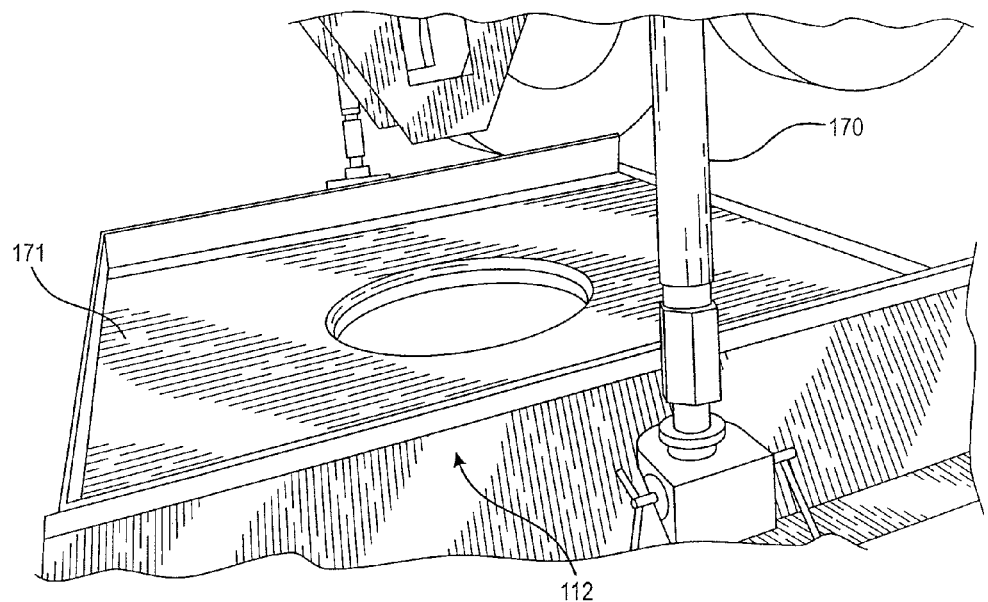
FIG. 5A is a perspective view of an enlarged perspective view of the top side of the confining plate assembly shown in FIG. 3B.
Figure 5B:
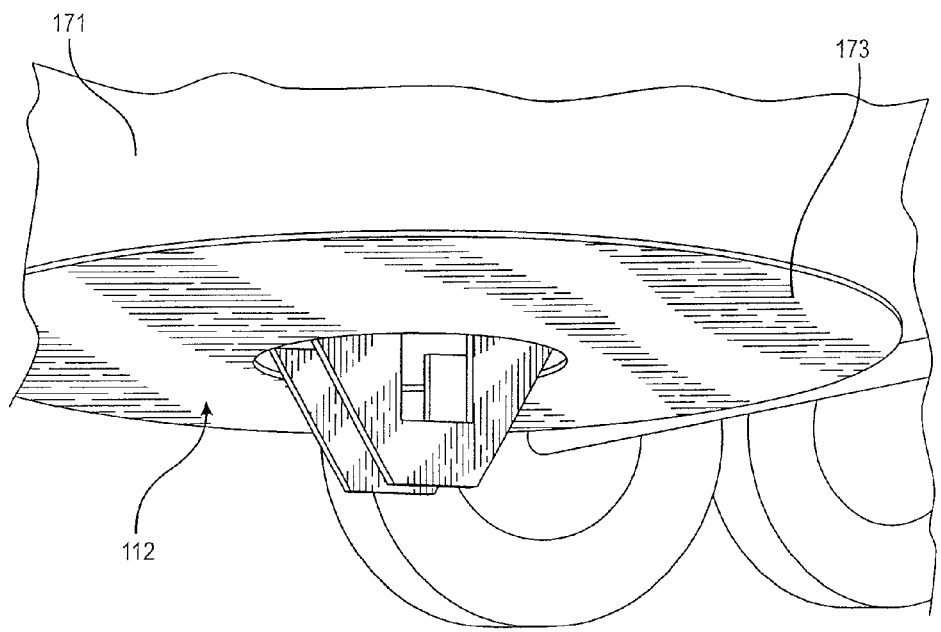
FIG. 5B is an enlarged perspective view of the bottom side of the confining plate assembly shown in FIG. 3B.

Referring to FIGS. 5A and 5B, a confining plate assembly 112 having a confining plate 171 applies vertically oriented confining stress to the ground around the perimeter of the bearing plate 111. The confining stress is typically controlled to between 0 and 6 pounds per square inch, and up to pounds per square inch, using two hydraulic or pneumatic cylinders 170, and can be applied incrementally during a test to evaluate the influence of confining stress on the tested soil.

The top of confining plate 171 provides rigidity, and contacts the cylinders 170. The bottom side of confining plate 171 includes a bottom plate 173, which is circular (see FIG. 5B). Only the bottom plate 173 is in contact with the ground during testing. The diameter of the bottom plate 173 is typically approximately 36 inches, with an aperture at the center thereof to receive the bearing plate 111. A rubber pad can be used at the contact of the bottom plate 173 and the ground surface to provide a uniform contact stress on rough ground.

FIG. 6 shows a 300 mm diameter 75 mm versine curved plate 111D in the test position in conjunction with the reference beam assembly 113. The curved plate 111D is connected to the adapter plate 161 with the integrated pick up plate 172. The reference beam 162 is in position to provide the reference point for bearing plate deformation measurement.

Figure 11A:
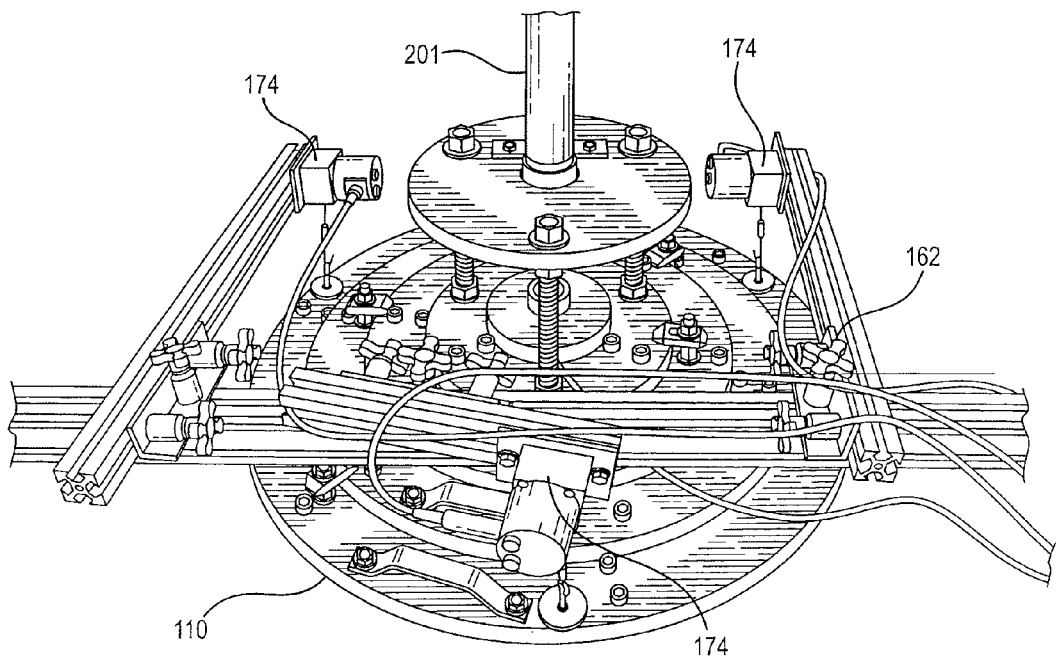
FIG. 11A is a top perspective view of the bearing plate assembly and piston shown in FIGS. 8A and 8B in conjunction with displacement transducers.
Figure 11B:
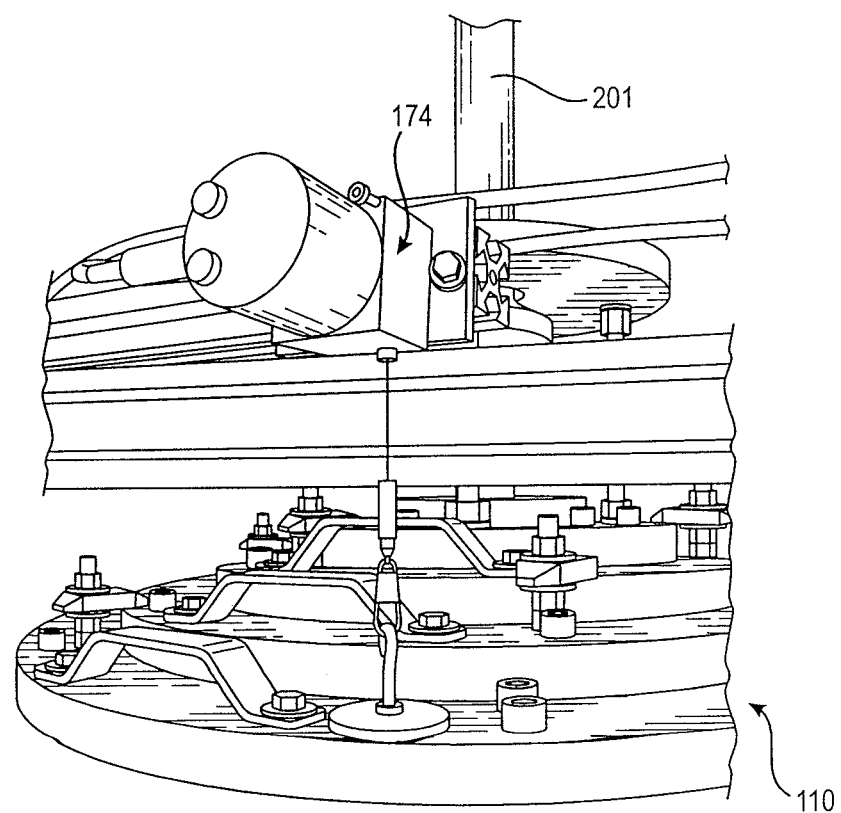
FIG. 11B is an enlarged perspective view of one of the displacement transducers shown in FIG. 11A.

See also FIGS. 11A and 11B, which show the bearing plate assembly 110 and piston 201 shown in FIGS. 8A and 8B in conjunction with a plurality of deflection sensors 174, here configured as draw wire displacement transducers. FIG. 11B is an enlarged view of one of the displacement transducers 174 shown in FIG. 11A.

The three or four draw wire displacement transducers 174 are positioned to determine the average vertical movement of the bearing plate, and bearing plate rotation. More specifically, the transducers 174 measure the deflection of the ground surface (i.e., via the bearing plate) at each increment of increased force applied by piston 201. The pick up plate 172 is not fixed rigidly to the piston collar 202. Rather, the pickup plate 172 is configured to be able to rotate with the bearing plate 111, and, as such, is not constrained by the piston 201.

More specifically, the displacement transducers 174 are connected to the reference beam 162 and positioned over the bearing plate 111 at an outer edge thereof spaced 120 degrees apart (see FIG. 11A) and at the center (not shown). The displacement transducers 174 provide an output signal to a data logger (not shown).

Figure 9:
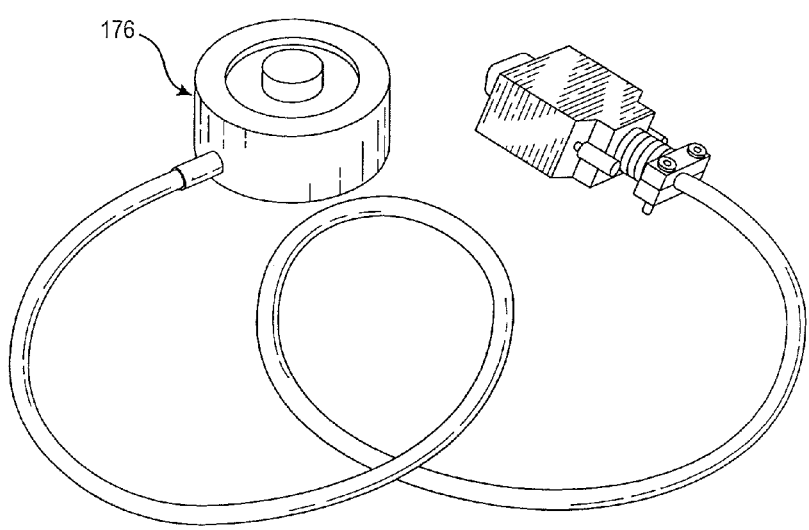
FIG. 9 is a top perspective view of a load cell associated with the bearing plate assembly and piston shown in FIGS. 8A and 8B.

A load cell 176 (see FIG. 9) is positioned directly at the center of the circular bearing plate 111D (see FIG. 10) and is acted on by a loading button (not shown) attached to the end of the hydraulic piston rod 201.

Figure 7A:
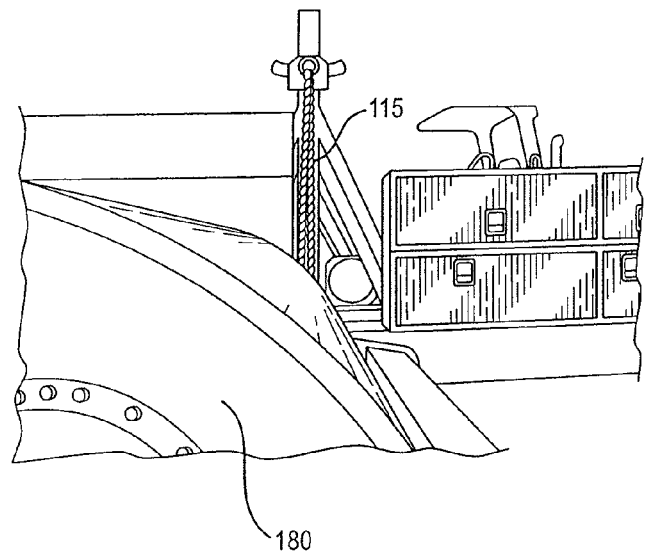
FIG. 7A is a perspective view of an integrated tie-down system for anchoring the mobile trailer system shown in FIG. 1.
Figure 7B:
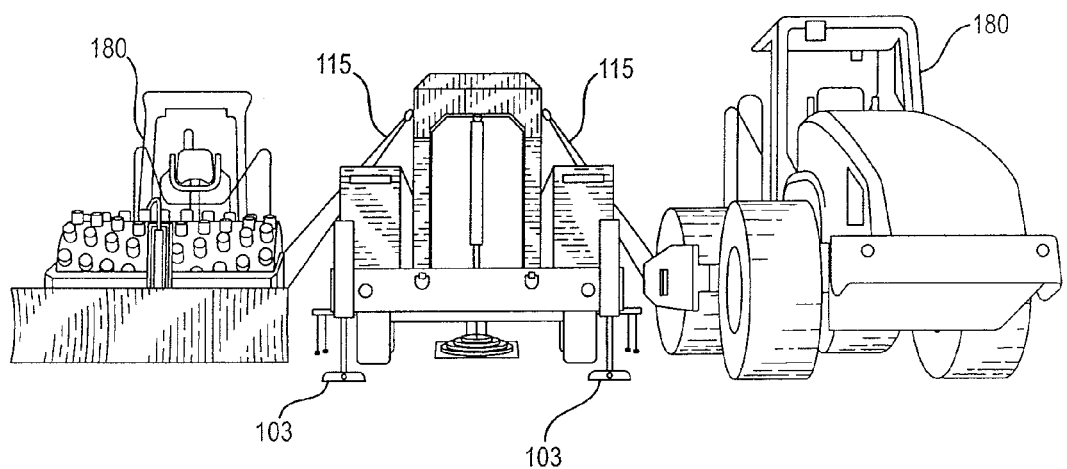
FIG. 7B is a perspective view of leveling jacks associated with the integrated tie-down system shown in FIG. 7A.
Figure 7C:
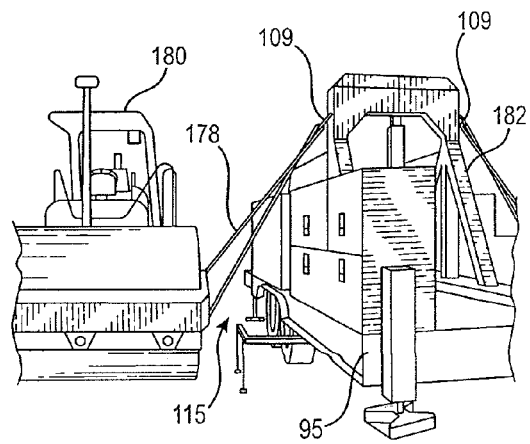
FIG. 7C is another perspective view of the integrated tie-down system for anchoring the mobile trailer system.

FIGS. 7A, 7B, and 7C show one embodiment of the integrated tie-down system 115 used to achieve a vertical reaction load of about 40,000 pounds. A turnbuckle and chain or cable 178 connect the trailer 95 to a heavy piece of construction equipment 180 positioned on each side of the trailer 95. By positioning the connection points at tie-down anchors 109 on the trailer 95 at the top sides of the derrick 182 (see FIGS. 1 and 3A), the down force in maximized. By positioning the heavy equipment 180 perpendicular to the trailer and derrick 182, the horizontal force in the longitudinal direction is minimized. As an alternative to using heavy construction equipment, either driven or screw-in earth anchors can be used at the derrick location and/or corners of the trailer.

Bearing plate tests are performed in increments of applied vertical load while monitoring bearing plate position relative to the reference beam (where the reference beam is positioned outside the deflection basin) and the rate of movement of the bearing plate. In another embodiment of the test method, similar tests can be performed with confining stress applied to the ground around the bearing plate. According to one embodiment of the invention, cyclic tests are performed by imparting a load pulse for a duration of approximately 1 to 60 seconds and releasing the load for a dwell time of approximately 1 to 60 seconds. That is, the load-unload cycle can vary from about 1 second to about 60 seconds per cycle. Cyclic load tests can be performed in combination with the confining plate up to 10,000 cycles or more of applying and releasing the load. Results for the tests are used to calculate the in situ stress-dependent stiffness, resilient modulus, and bearing capacity of the soils and geo-materials.

According to another embodiment of the invention, the mobile test system and associated methods facilitate below ground testing. With below ground testing, the test is performed in an excavation at an elevation below the ground surface. According to the aforementioned AASHTO T222, tests performed at the ground surface are referred to as "unconfined," while tests performed below the ground surface are referred to as "confined."

The following examples illustrate further aspects of the invention.

EXAMPLE I

Bearing plate tests were performed using the mobile test system 101 in accordance with the present invention at a test site in Iowa on a control test section of a nominal six inches of a crushed limestone aggregate base overlying a lean clay subgrade. The tests were conducted using a 300 mm diameter flat bearing plate without a confinement plate. The bearing plate tests were conducted both on the control section, and on a similar section of ground reinforced with a Tensar® TX160 geogrid. The geogrid reinforcement is commercially available from Tensar International Corporation of Alpharetta, Ga. The test methods used and the methods of their use were consistent with the disclosure provided herein. The testing was designed to compare the load versus deflection characteristics of the control section with that of the geogrid section in accordance with the present invention to determine the ground stiffness and bearing capacity thereof.

Figure 12:
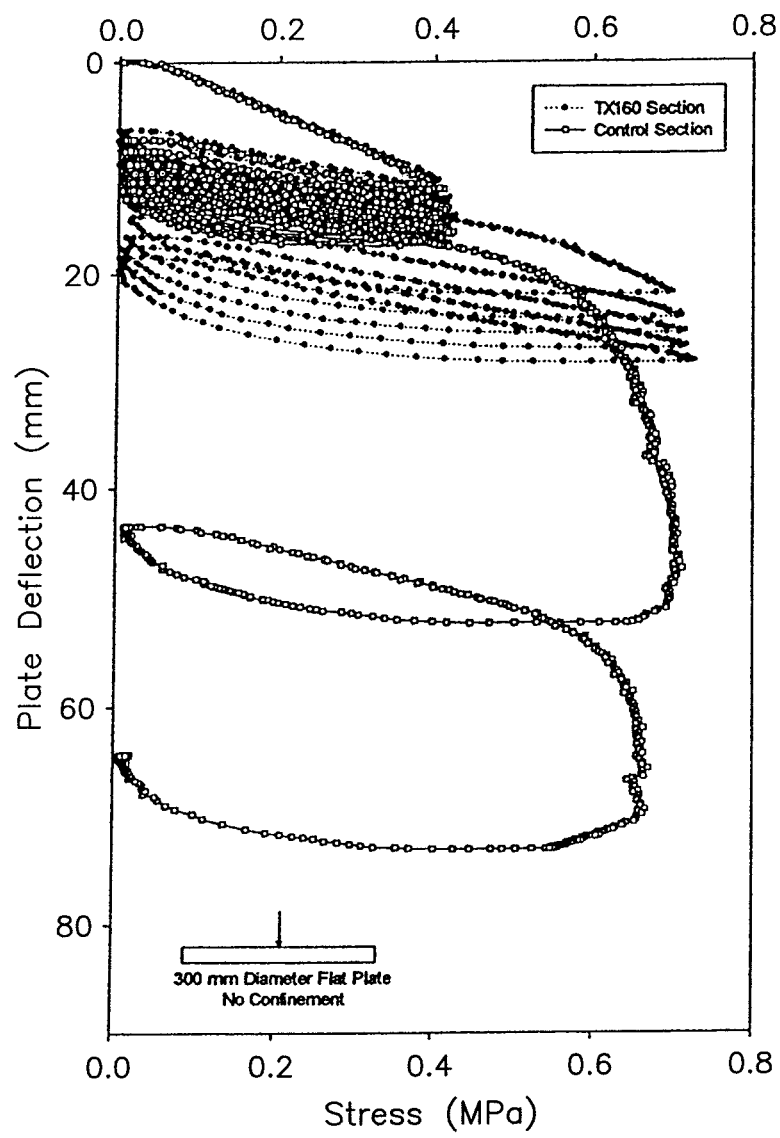
FIG. 12 is a graph depicting test results obtained with the mobile trailer system shown in FIG. 1 for a flat plate bearing test with no confinement.

The results presented in FIG. 12 demonstrate the ground deformation (i.e., as determined by bearing plate deflection) associated with five repetitive load-unload cycles between 0 and 0.4 MPa for both test sections, and two and five additional cycles between 0 and 0.75 MPa for the control section and geogrid reinforced section, respectively. The tests were conducted by increasing the application load at a relatively constant rate using the hydraulic control system. Results from the initial and reload curves are used to determine the stiffness calculated as the plate contact stress divided by the vertical deformation (i.e., plate deflection measured in mm) and the bearing capacity at the inflection point where the deformation rate increases. As used herein, the term "stiffness" is equal to change in stress/change in deflection. The first load cycle yields more deflection for a given stress range compared to subsequent load cycles.

The results from the Example I tests demonstrate the increase in bearing capacity that is realized from incorporating the geogrid relative to the control section with no geogrid. The bearing capacity of the control section was about 0.62 MPa, while the bearing capacity of the geogrid section was not reached even at the maximum applied stress for this test (0.75 MPa). After applying the final load-unload cycle, the permanent deformation for the control section was about 65 mm, and for the geogrid reinforced section was only about 20 mm.

EXAMPLE II

In this test, bearing plate tests were performed using a 300 mm diameter curved plate (75 mm versine) as shown in FIGS. 4A and 6. The tests were performed using the mobile test system 101 in accordance with the present invention at a test site in Iowa on a control test section of a nominal six inches of a crushed limestone aggregate base overlying a lean clay subgrade. Bearing plate tests were conducted on the control section and on a similar section having the Tensar® TX160 geogrid reinforcement.

Figure 13A:
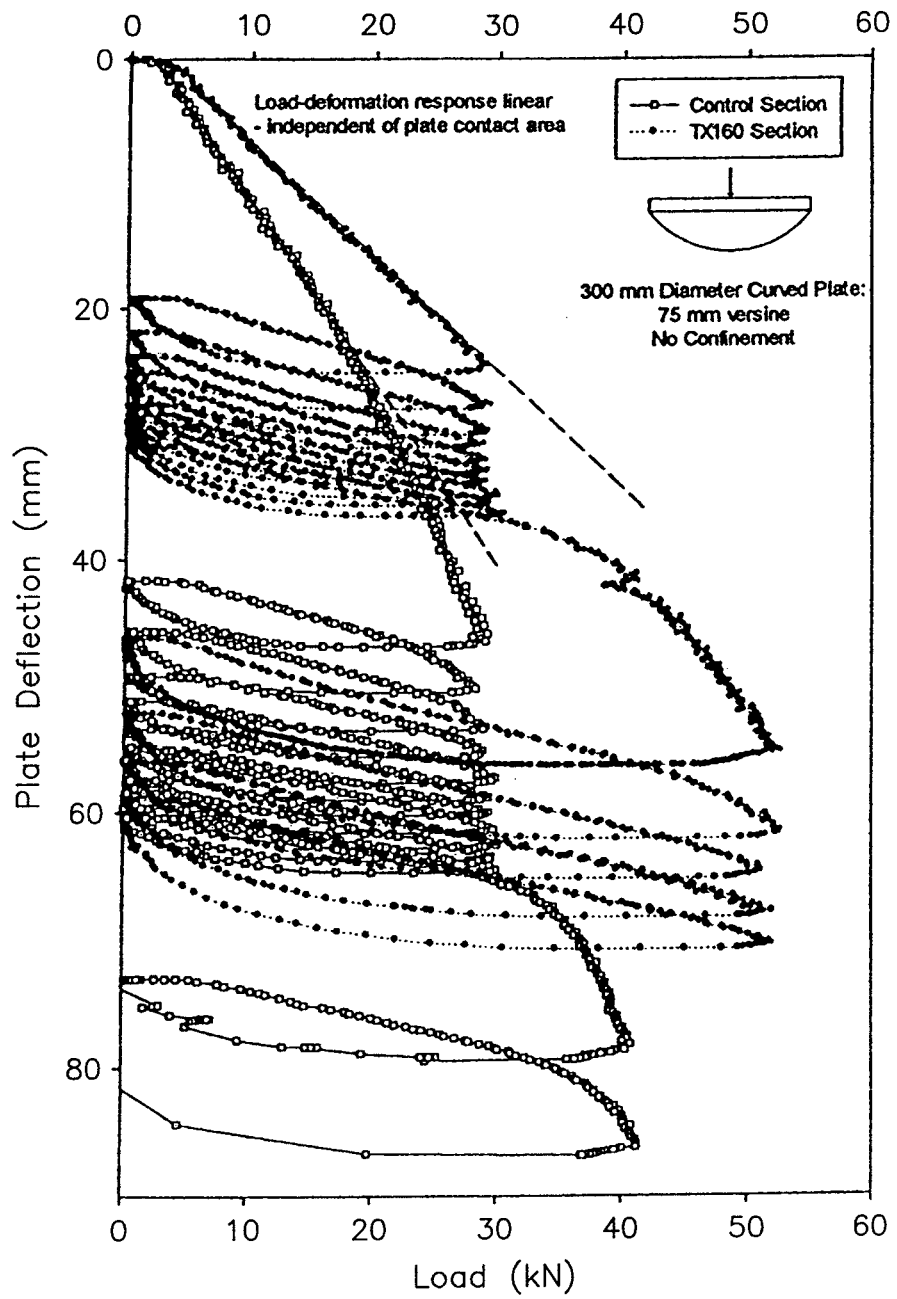
FIG. 13 presents graphs depicting test results obtained with the mobile trailer system shown in FIG. 1 for a curved plate bearing test with no confinement: (a) load versus deformation; and (b) plate contact stress versus deformation.

Results from the test are presented in FIGS. 13 (a) and (b). For each of the tests, the curved bearing plate was seated into the ground to generate a vertical indention equal to about 20 mm. The load versus deflection results (FIG. 13(a)) demonstrate a near linear response during the initial load cycle for the control section up to about 17 kN, whereas for the geogrid reinforced section a near linear response is observed up to about 29 kN. The stiffer response of the geogrid reinforced section demonstrates the resistance to deformation for the radially oriented stresses at the contact surface of the curved plate.

Figure 13B:
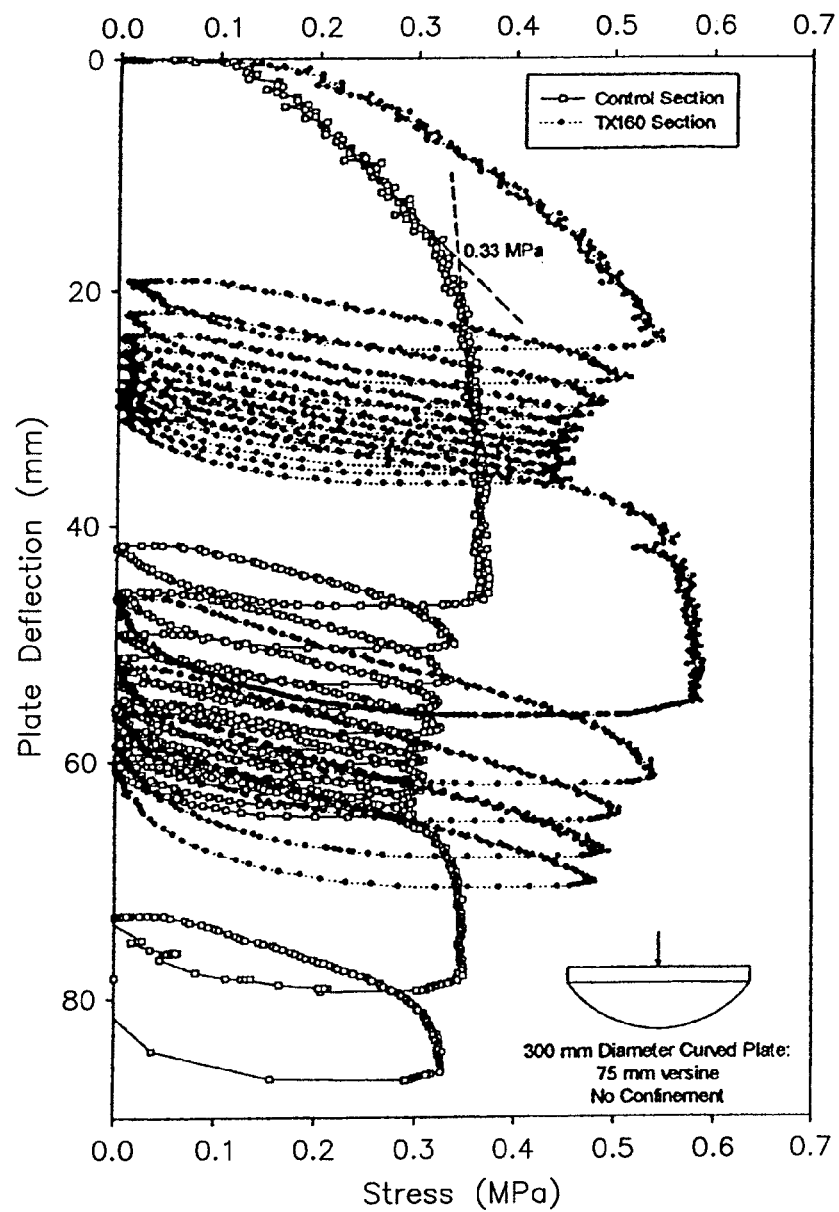

Plotting the results from the tests in FIG. 13(b) as stress versus load, where stress is the load divided by the plate-ground contact area, demonstrates that the bearing capacity of the control section is about 0.33 MPa, and of the geogrid section is about 0.56 MPa. Using the curved bearing plate for this test demonstrated the use of oriented stress testing to study the ground reinforcing mechanism.

EXAMPLE III

In this example, two bearing plate tests were performed using the 300 mm diameter curved bearing plate (38 mm versine). Using the mobile test system 101 in accordance with the present invention, the tests were performed both with and without the confining plate, which provides controlled and uniform contact with the ground around the bearing plate. In this example, the internal diameter of the confining plate was 13 inches (330 mm) and the external diameter was 36 inches (915 mm). A 0.5 inch thick low durometer rubber pad was used to provide uniform stress transfer from the bottom of the confining plate to the ground.

Figure 14:
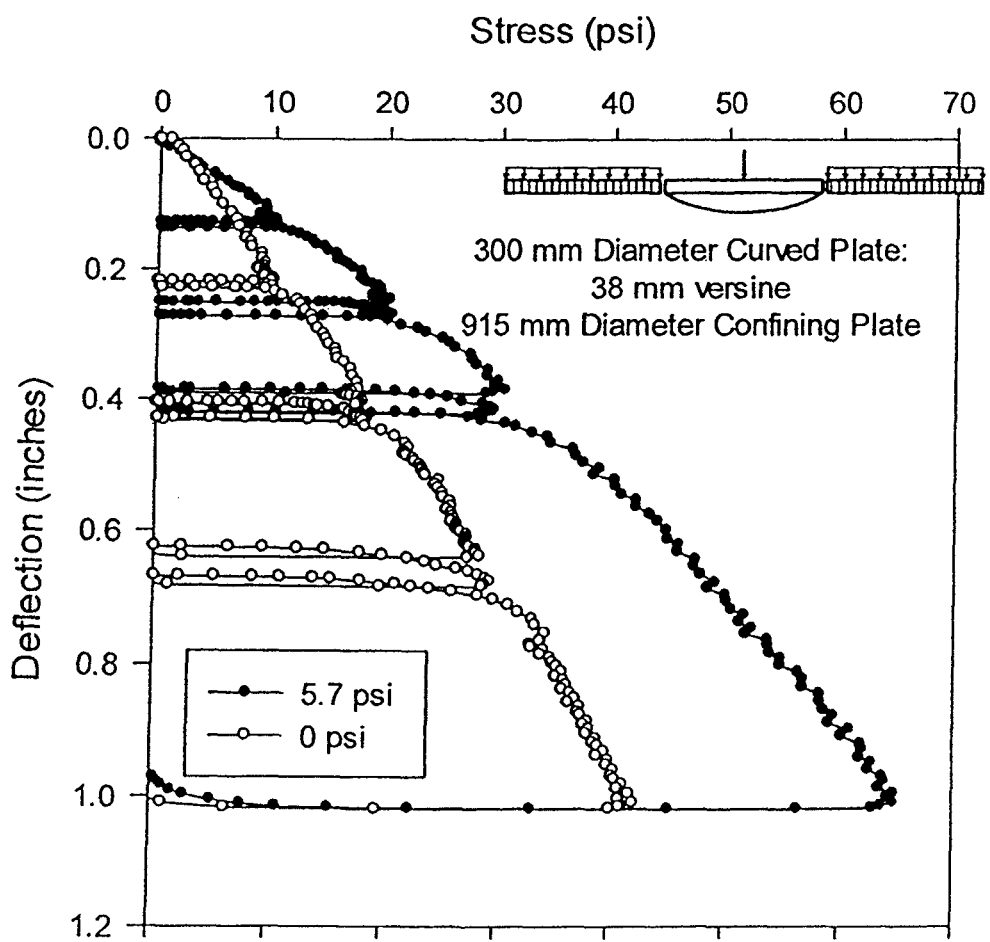
FIG. 14 is a graph depicting test results obtained with the mobile trailer system shown in FIG. 1 for a curved plate bearing test with and without confinement.

FIG. 14 shows the deflection versus plate contact stress results for tests performed on a controlled test section with a nominal 12 inches of crushed limestone over a soft lean clay subgrade. As shown in FIG. 14, the test compared the effect on deflection of applying a confining stress of a nominal 5.7 pounds per square inch (as designated by the legend "—●—") with that of no confining stress (designated by the legend "—○—"). Comparing the results of the two tests, the test with the 5.7 pounds per square inch of vertical confinement stress produced a stiffer response than the test with no confining stress. The confining stress for this test represents the stress that would be anticipated below the bottom of a concrete pavement layer. The modulus of subgrade reaction for the test without confinement is about 44 pounds per cubic inch.

By comparison, with confinement to simulate bottom of pavement stress conditions, the modulus of subgrade reaction increases to 82 pounds per cubic inch.

By performing bearing plate tests at multiple plate confining stresses and plate contact stresses, a mathematical relationship between ground stiffness and confinement can be calculated. Generally, the calculations that determine the modulus of subgrade reaction, for example, are referred to in the art as "confining stress dependent stiffness or modulus" calculations. There are, of course, different mathematical formulas that correspond to the various test methods used. For example, the aforementioned AASHTO T307 is a reference standard test, but requires special testing in a laboratory environment on special samples sizes.

The present invention, however, is novel in that it can apply and control the confining stress in-situ on the undisturbed ground. See, for example, FIG. 18, which shows the in situ resilient modulus resulting from a cyclic test sequence with various combinations of plate stress and confining plate stress. The results of the test sequence depicted in FIG. 18 can be presented as a mathematical relationship between plate stress, bulk stress, and in situ resilient modulus. For this test, the in situ resilient modulus was calculated as the ratio of the cyclic stress divided by the recoverable displacement (during unloading) using the following equation:

$$Mr = \frac{(1-v^2) \cdot r \cdot \Delta\sigma_p}{\delta_c} \cdot f$$

where Mr=in situ resilient modulus, $\delta_c$ is the recoverable deflection during the unloading portion of the cycle, v is the Poisson ratio (assumed as 0.4), $\Delta\sigma_p$ is the cyclic stress, r is the radius of the plate and f is the shape factor selected as 2 assuming a uniform stress distribution under a circular rigid plate.

Figure 18A:
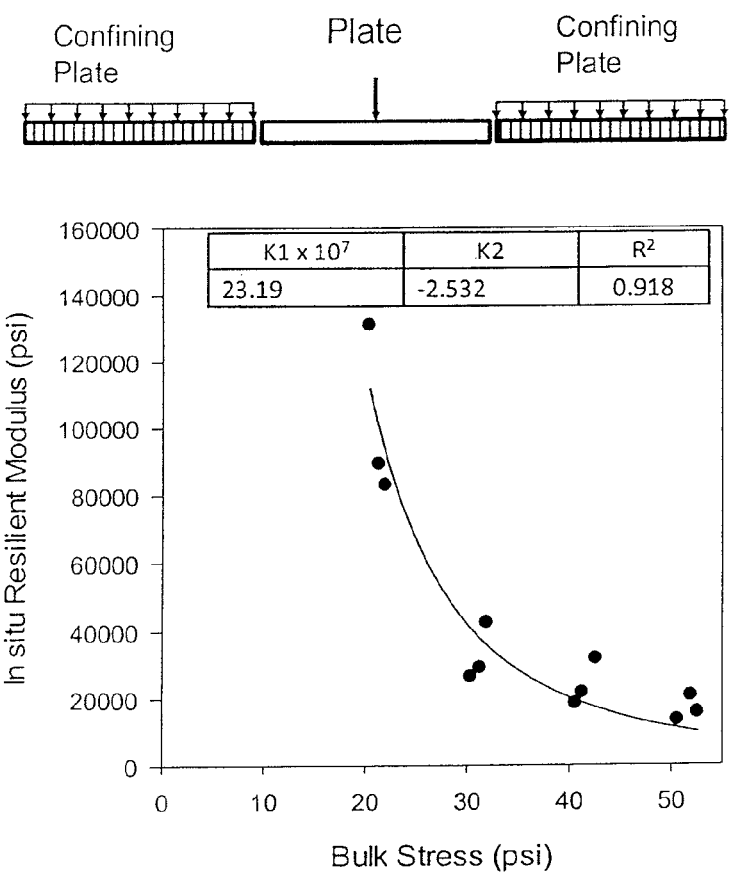
FIG. 18 presents graphs depicting test results obtained with the mobile trailer system shown in FIG. 1: (a) in situ resilient modulus versus bulk stress for tests performed with (b) combinations of plate stress and confining stress.

A bulk stress model was used to generate values of model parameters according to the following formula:

$$Mr = k1(\sigma p_p + k\sigma_c)^{k2}$$

where Mr=in situ resilient modulus, as above in the equation for calculating the in situ resilient modulus, where k1 and k2 are empirical parameters, $\sigma_p$=the maximum cyclic plate contact stress, $\sigma_c$=plate confining stress, and k=lateral earth pressure coefficient. FIG. 18 shows the tests results using the average Mr value for the last 5 cycles of a 20 cycle sequence for each combination of plate stress and confining stress.

EXAMPLE IV

In another test using the mobile test system 101 in accordance with the present invention, a 12 inch diameter flat bearing plate without confinement was used to determine the in situ static modulus of subgrade reaction in accordance with the aforesaid test standard AASHTO T222. Tests were performed by incrementally increasing the plate contact stress and maintaining the contact stress while monitoring average plate deflection. For a given stress increment, once the rate of plate movement was equal to 0.001 inch/minute for three consecutive minutes, the next stress increment was applied.

Figure 15A:
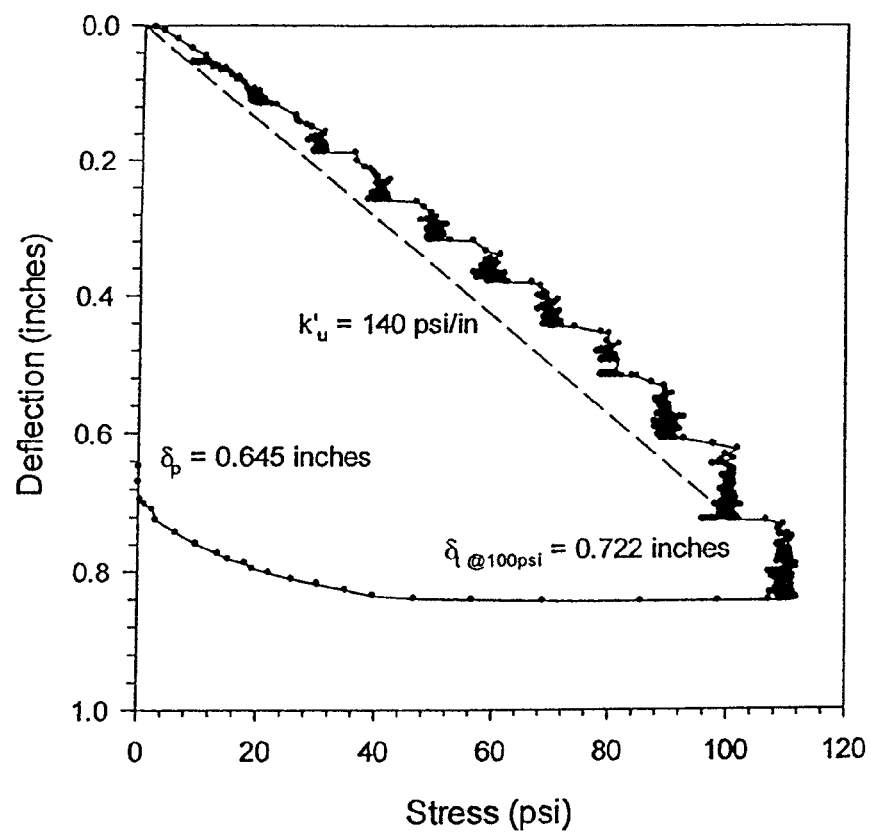
FIG. 15 presents graphs depicting incremental static test results obtained with the mobile trailer system shown in FIG. 1 for a flat plate bearing test without confinement: (a) stress versus deflection response; and (b) deflection versus time response.
Figure 15B:
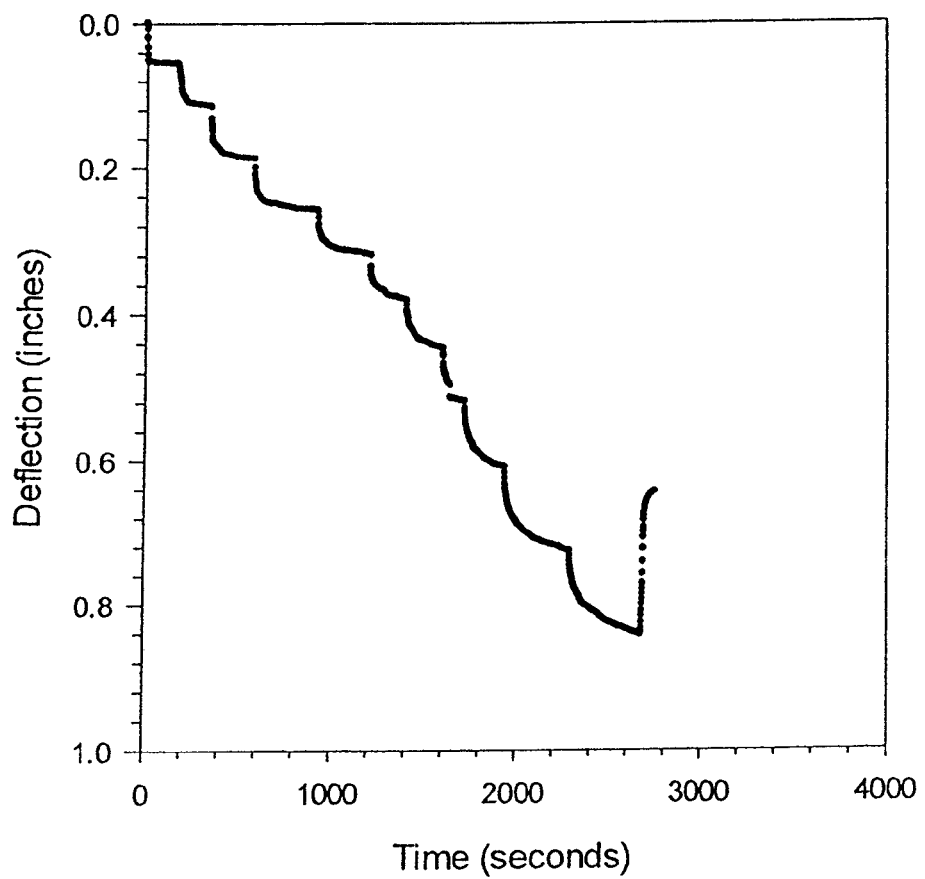

The results in FIG. 15 show the plate contact stress versus vertical deflection plot and the vertical deflection versus time plot, FIGS. 15(a) and (b), respectively. The material tested in this example was a nominal 12 inches of compacted reclaimed hydrated fly ash supported by a salty sand subgrade with a CBR value of about 8. The TX160 geogrid reinforcement was placed at the surface of the subgrade prior to placement and compaction of the reclaimed fly ash material. The uncorrected modulus of subgrade reaction for this test was calculated to be 140 pounds per cubic inch, and at a plate contact stress of 100 pounds per square inch the maximum plate deflection was 0.722 inches. After unloading the plate, the final permanent deflection was determined to be 0.645 inches.

EXAMPLE V

Figure 16A:
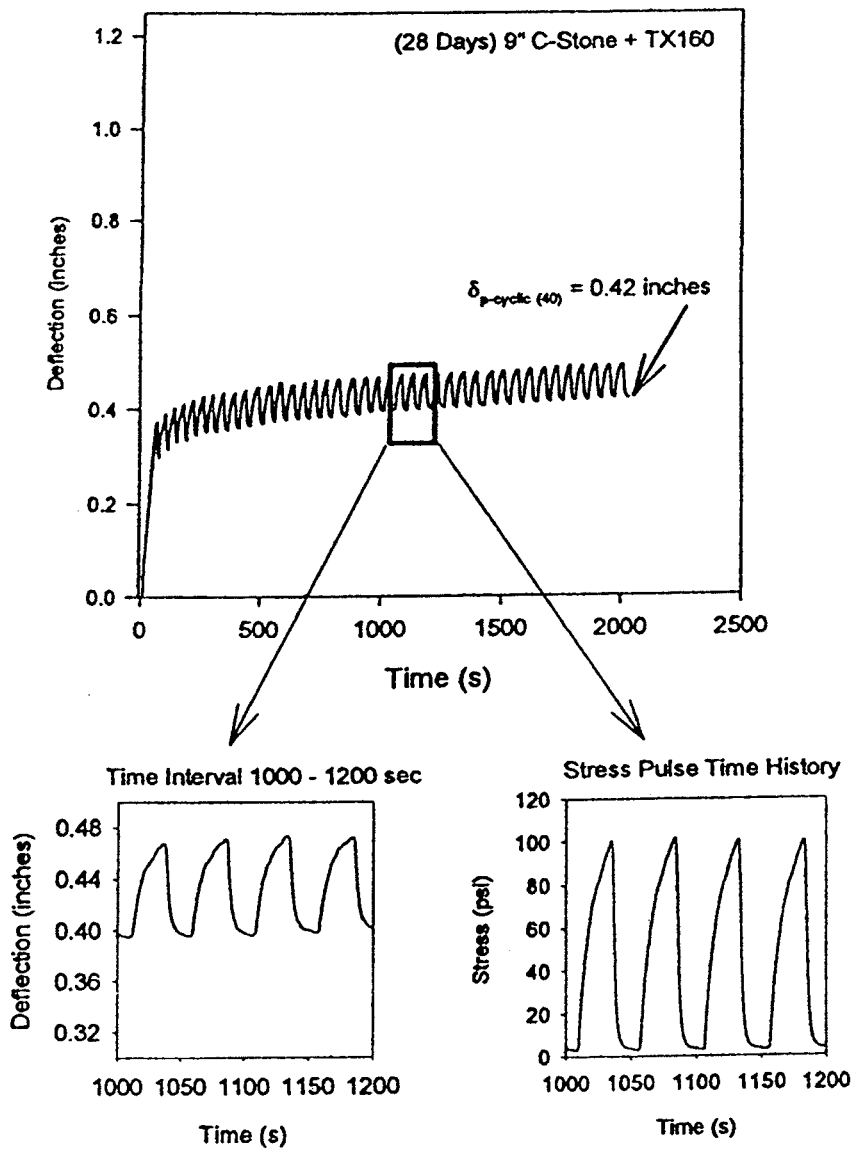
FIG. 16 presents graphs depicting cyclic test results obtained with the mobile trailer system shown in FIG. 1 for a flat plate bearing test without confinement: (a) deflection versus time; (b) stress versus deflection; and (c) resilient modulus and permanent deflection versus the number of load cycles.

In still another test, the mobile test system 101 in accordance with the present invention was used to determine the in situ permanent deflection and resilient modulus of the ground. FIG. 16 shows the relationships determined from a controlled cyclic stress test with 40 cycles of load-unload. FIG. 16(a) shows the relationship between deformation and time, and highlights the stress versus time and deflection (i.e., deformation) versus time for a few representative load cycles.

In this test, the maximum applied plate contact stress for the 12 inch flat plate was about 100 pounds per square inch and the minimum applied stress during unloading was about 2 pounds per square inch. The load-unload cycle time was set to about 50 seconds for this test.

Figure 16B:
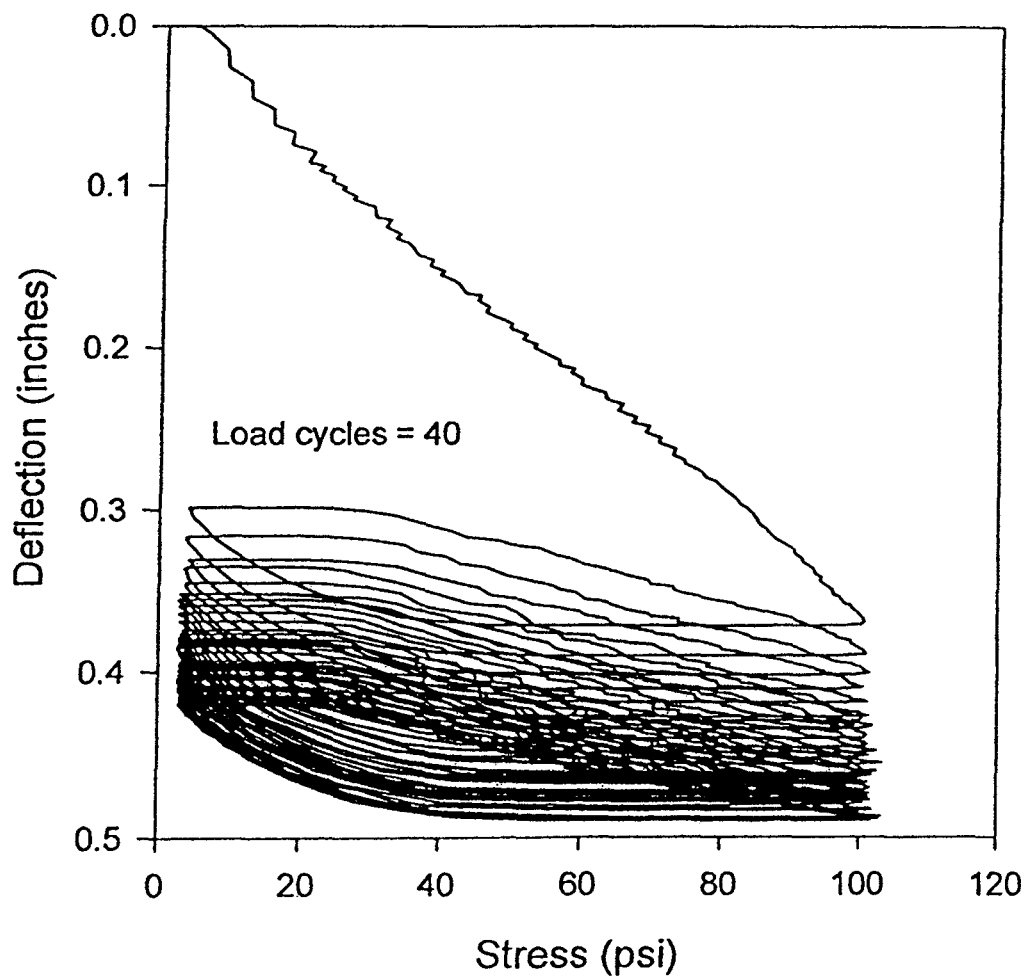

FIG. 16(b) shows the plate contact stress versus deflection relationship. The load-unload behavior is captured as hysteresis loops demonstrating increasing deflection with increasing number of load-unload cycles and the increase in stiffness after completing the first load-unload cycle. The results show that the permanent deflection increased from zero to about 0.31 inches after the first load-unload cycle and increased to 0.42 inches after the final load-unload cycle.

Figure 16C:
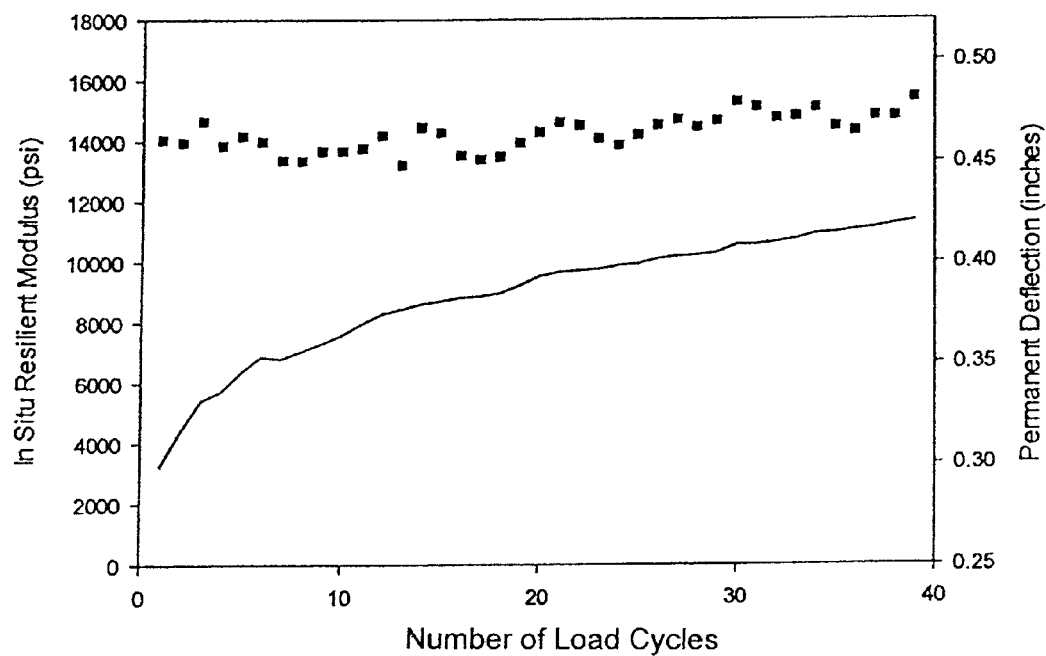

FIG. 16(c) shows both the relationship between permanent deflection and the number of load-unload cycles, and the relationship between resilient modulus (calculated as a function of the applied stress divided by the recoverable deflection) and the number of load-unload cycles. The in situ resilient modulus for this test was about 14,000 pounds per square inch.

The results of the above-described Examples I-V demonstrate that advantages associated with the present invention relative to the prior art include, inter alia, the real time data collection and calculation of resilient modulus, subgrade support, and bearing capacity. Importantly, the aforementioned information can then be used for corrective action, quality control, and quality assurance throughout the foundation construction process. Further, the equipment is able to simulate final/post construction stress conditions at the point of testing through the active application of surface confinement and plate geometry.

The present invention is advantageous because it integrates mobility, a ground preparation tool, self weight, ballast, and tie-down anchor connections for developing reaction weight, and controlled ground stresses or deflections from the bearing plates and confining plate system. Tests can be performed to evaluate the static stress-deflection relationship and the cyclic stress-deformation (i.e., deflection) behaviors and bearing capacity as a function of ground confinement.

The foundation systems to which the various embodiments of the present invention would be applicable include, but are not limited to, airfields, paved and unpaved roads and highways, residential and commercial buildings, storage and intermodal facilities, rail systems, and the like.

It is not intended that the present invention be limited to the specific embodiments described herein. The foregoing is considered as illustrative only of the principles of the invention. For example, although the mobile test system and associated test methods have been described as being configured for use in the foundation construction applications described herein, the mobile test system and the test methods could be employed in other services in which the various features of the invention would be beneficial.

Further, since numerous modifications and changes will readily occur to those skilled in the art, it is not desired to limit the invention to the exact construction and operation shown and described, and, accordingly, all suitable modifications and equivalents may be resorted to, falling within the scope of the invention.

What is claimed is:

1. A mobile test system for determining properties of a soil or geo-material, comprising:
a component that prepares ground containing the soil or geo-material for testing;
a component that applies static or cyclic loading to one or more bearing plates of various geometries positioned at a ground surface or below the ground surface to determine stress and deflection dependent stiffness relationships and bearing capacity of the soil or geo-material;
a confining plate system configured to be positioned adjacent the one or more bearing plates and at the ground surface or below the ground surface; and
a control system configured to apply controlled force to the confining plate system such that the confining plate system applies a substantially uniform and constant stress to the ground adjacent the one or more bearing plates.

2. The mobile test system according to claim 1, further comprising a system with hydraulic lifting jacks positioned to be outside a deflection basin from a bearing plate test.

3. The mobile test system according to claim 2, wherein the mobile test system is configured as a trailer, and wherein a reaction from the bearing plate test is a weight of the trailer.

4. The mobile test system according to claim 3, wherein the reaction from the bearing plate tests is increased by ballast-containing boxes attached to the trailer.

5. The mobile test system according to claim 3, wherein the reaction from the bearing plate tests is increased using a tie-down system positioned in conjunction with at least one of a derrick assembly and corners of the trailer.

6. The mobile test system according to claim 5, wherein the tie-down system uses construction equipment as a reaction source.

7. The mobile test system according to claim 5, wherein the tie-down system uses drilled or driven earth anchors as a reaction source.

8. The mobile test system according to claim 3, wherein the trailer is movable with a crane using anchor connections near corners of the trailer.

9. The mobile test system according to claim 1, wherein the system is balanced front to rear by a moveable counterweight assembly.

10. The mobile test system according to claim 9, wherein the counterweight assembly (i) is used as a tray for a bearing plate assembly and (ii) for plate changeout, slides under the component that applies the static or cyclic loading to the bearing plates.

11. The mobile test system according to claim 9, wherein the bearing plate assembly includes a pick-up adapter for various plate geometries and assemblies.

12. The mobile test system according to claim 11, wherein the bearing plate assembly includes a bearing plate having a shape that is flat, conical, spherical, wedge, conical frustum, truncated frustum, or cycloid.

13. The mobile test system according to claim 12, wherein the bearing plate shape is selected to achieve a stress orientation in the soil or geo-material that is at least one of vertical, horizontal, radial, tangential, and circumferential.

14. The mobile test system according to claim 9, wherein the counterweight assembly is secured in place using a brake system and locking pins.

15. The mobile test system according to claim 1, wherein the device that prepares the soil or geo-material for testing is an integrated plow system.

16. The mobile test system according to claim 1, further comprising an integrated confining plate system to provide uniform and constant stress to the ground adjacent the main bearing plate test.

17. The mobile test system according to claim 16, wherein the integrated confining plate system is secured to a counterweight assembly that balances the system.

18. The mobile test system according to claim 17, wherein the confining plate system is integrated, and wherein the confining plate system is pressed onto the ground using pneumatic or hydraulic cylinders under controlled conditions.

19. The mobile test system according to claim 1, further comprising an independent and adjustable position reference beam to provide vertical position measurement of a bearing plate assembly placed on or in the ground.

20. The mobile test system according to claim 1, further comprising a component that applies ground confining stress conditions independent of bearing plate loading.

21. A method of performing a static bearing plate test of a soil or geo-material, comprising the following steps:
preparing a ground surface using an integrated plow system;
positioning a bearing plate assembly on or in the ground;
applying controlled loads on or in the ground via the bearing plate assembly using a hydraulic control system or controlled deflection measurements using a vertical deformation response during loading;
positioning a confining plate system adjacent the bearing plate assembly and at a ground surface or below the ground surface; and
applying controlled force to the confining plate system such that the confining plate system applies a substantially uniform and constant stress to the ground adjacent the bearing plate assembly.

22. The method according to claim 21, further comprising, before the application of the controlled loads, applying controlled ground confinement using the confinement plate system.

23. A method of performing cyclic plate bearing test of a soil or geo-material, comprising the following steps:
preparing a ground surface using an integrated plow system;
positioning a bearing plate assembly on or in the ground; and
applying controlled load-unload cycles on or in the ground via the bearing plate assembly using a hydraulic control system or controlled deflection measurements using the vertical deformation response during loading;
positioning a confining plate system adjacent the bearing plate assembly and at a ground surface or below the ground surface; and
applying controlled force to the confining plate system such that the confining plate system applies a substantially uniform and constant stress to the ground adjacent the bearing plate assembly.

24. The method according to claim 23, further comprising, before the application of the controlled load-unload cycles, applying controlled ground confinement using the confinement plate system.

25. The method according to claim 24, wherein stress and deformation results are used to determine an in situ resilient modulus of the ground as a function of applied bearing plate stress, recoverable deformation of the bearing plate, and a quantity of load-unload cycles.

26. The method according to claim 24, wherein a confining stress dependent in situ resilient modulus is determined as a function of the applied confining stress, the bearing plate stress, the recoverable deformation of the bearing plate, and the quantity of load-unload cycles.

27. A mobile test system configured as a trailer for determining properties of a soil or geo-material, the mobile test system comprising:
a hydraulic piston with a control system and derrick frame for applying static and cyclic loads to ground containing the soil or geo-material;
a reference beam for bearing plate position measurements and deflection controlled testing;
a moveable counterbalance weight system for balancing the trailer prior to bearing plate loading;
an integrated plow to prepare the ground for testing; a hydraulic or pneumatic confining plate system to control ground stresses independent of the bearing plate stresses;
a bearing plate that induces controlled stress magnitude and stress orientation in the soil or geo-material;
a confining plate system configured to provide apply a substantially vertical load to a confining plate positioned adjacent the bearing plate and soil or geo-material; and
a control system configured to apply controlled force to the confining plate system such that the confining plate system applies a substantially uniform and constant stress to the ground adjacent the bearing plate.

28. A mobile test system for determining properties of a soil or geo-material, the mobile test system comprising:
a component that applies static or cyclic loading to one or more bearing plates of various geometries positioned at a prepared ground surface or below the ground surface to determine stress and deflection dependent stiffness relationships and bearing capacity of the soil or geo-material;
a confining plate system configured to provide apply a substantially vertical load to a confining plate positioned adjacent the one or more bearing plates and at the prepared ground surface or below the ground surface; and
a control system configured to apply controlled force to the confining plate system such that the confining plate system applies a substantially uniform and constant stress to the ground adjacent the one or more bearing plates.

* * * * *